United States Patent
Gokaraju et al.

(10) Patent No.: US 12,138,288 B2
(45) Date of Patent: Nov. 12, 2024

(54) SYNERGISTIC HERBAL COMPOSITIONS FOR TESTOSTERONE BOOSTING

(71) Applicant: LAILA NUTRACEUTICALS, Vijayawada (IN)

(72) Inventors: Ganga Raju Gokaraju, Vijayawada (IN); Rama Raju Gokaraju, Vijayawada (IN); Kiran Bhupathiraju, Vijayawada (IN); Trimurtulu Golakoti, Vijayawada (IN); Venkata Kanaka Ranga Raju Gokaraju, Vijayawada (IN); Venkateswarlu Somepalli, Vijayawada (IN); Venkata Krishna Raju Alluri, Vijayawada (IN)

(73) Assignee: LAILA NUTRACEUTICALS, Vijayawada (IN)

( * ) Notice: Subject to any disclaimer, the term of this patent is extended or adjusted under 35 U.S.C. 154(b) by 493 days.

(21) Appl. No.: 17/054,079

(22) PCT Filed: May 8, 2019

(86) PCT No.: PCT/IN2019/050361
§ 371 (c)(1),
(2) Date: Nov. 9, 2020

(87) PCT Pub. No.: WO2019/215755
PCT Pub. Date: Nov. 14, 2019

(65) Prior Publication Data
US 2021/0236572 A1    Aug. 5, 2021

(30) Foreign Application Priority Data
May 8, 2018   (IN) ............................. 201841017306

(51) Int. Cl.
| | |
|---|---|
| A61K 36/185 | (2006.01) |
| A23L 33/105 | (2016.01) |
| A23L 33/24 | (2016.01) |
| A61K 31/522 | (2006.01) |
| A61K 31/7048 | (2006.01) |
| A61K 45/06 | (2006.01) |
| A61K 47/38 | (2006.01) |
| A61P 5/24 | (2006.01) |

(52) U.S. Cl.
CPC .......... *A61K 36/185* (2013.01); *A23L 33/105* (2016.08); *A23L 33/24* (2016.08); *A61K 31/522* (2013.01); *A61K 31/7048* (2013.01); *A61K 45/06* (2013.01); *A61K 47/38* (2013.01); *A61P 5/24* (2018.01); *A61K 2236/333* (2013.01); *A61K 2236/51* (2013.01)

(58) Field of Classification Search
None
See application file for complete search history.

(56) References Cited

U.S. PATENT DOCUMENTS

| | | |
|---|---|---|
| 5,543,146 A | 8/1996 | Perez |
| 2006/0110415 A1 | 5/2006 | Gupta |
| 2010/0021533 A1 | 1/2010 | Mazed et al. |
| 2011/0065662 A1 | 3/2011 | Rinsch et al. |
| 2013/0164394 A1 | 6/2013 | Ferrari et al. |
| 2014/0086999 A1 | 3/2014 | Elistratov |
| 2017/0173100 A1 | 6/2017 | Antony |

FOREIGN PATENT DOCUMENTS

| | | | |
|---|---|---|---|
| CA | 2645419 | * | 9/2007 |
| WO | 2011026500 A1 | | 3/2011 |

OTHER PUBLICATIONS

PR Newswire, 2024.*
"Theobromine." Wikipedia, Wikimedia Foundation, Apr. 28, 2018; p. 1 (en.wikipedia.org/wiki/Theobromine.).
Written Opinion of the International Searching Authority re PCT/IN2019/050361 dated Oct. 14, 2019; 6 pgs.
PCT International Search Report re PCT/IN2019/050361 dated Oct. 12, 2019; 3 pgs.

* cited by examiner

*Primary Examiner* — Michael V Meller
(74) *Attorney, Agent, or Firm* — Kramer & Amado, P.C.

(57) ABSTRACT

Synergistic herbal compositions comprising combination of a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* for improving testosterone levels. The invention further provides the method of obtaining at least one health benefit related to enhanced anabolic and androgenic activities in the body selected from improving testosterone levels, energy levels, sustained energy, vigor, stamina, healthy aging, cellular longevity, muscle mass, muscle strength sexual function (libido and erectile function) and psychological well-being (mood and focus); and reducing stress in humans and alleviating the symptoms associated with the low levels of testosterone in humans such as loss of libido, loss of erectile function, abdominal obesity, decreased muscle mass and strength, fatigue, mood swing, decreased bone density, decreased motivation, and decreased memory and concentration.

13 Claims, 1 Drawing Sheet

SYNERGISTIC HERBAL COMPOSITIONS FOR TESTOSTERONE BOOSTING

TECHNICAL FIELD OF THE INVENTION

The invention relates to synergistic herbal compositions comprising at least one ingredient selected from the extracts and fractions derived from *Punica granatum* and at least one ingredient selected from the extracts and fractions derived from *Theobroma cacao* for improving testosterone levels in humans and/or alleviating at least one symptom/condition associated with lower than normal levels of testosterone hormone in humans. The invention also relates to the method of improving testosterone levels in humans and/or method of alleviating at least one symptom associated with low levels of testosterone hormone in humans.

BACKGROUND OF THE INVENTION

Testosterone is a hormone chemical messenger produced primarily by Leydig cells in testes and is responsible for the proper development of male sexual characteristics. It is a type of androgen essential for the process of spermatogenesis.

Testosterone is an anabolic hormone and known to regulate a number of functions in men in addition to sperm production, which include sex drive, bone mass, muscle growth, muscle strength, stamina, increased energy, mood etc. As men age, the serum testosterone levels gradually decrease resulting in various physical and mental changes such as loss of libido, loss of erectile function, abdominal obesity, decreased muscle mass and strength, fatigue, decreased bone density, mood swing, decreased motivation, and decreased memory and concentration.

Many Testosterone replacement therapies are available to treat the men suffering from testosterone deficiency, which include dehydroepiandrosterone (DHEA), and herbal products such as Tribulus *terrestris*. The low levels of testosterone were found to be associated with significantly lower levels of magnesium, iron, and zinc.

Hence, supplements containing these nutrients are also available as testosterone boosters.

The patent publication WO2011026500 A1 discloses compositions comprising extracts of Tribulus *terrestris* and *Lepidium meyenii* for the treatment of erectile dysfunction by increasing testosterone levels.

The patent publication US 20140086999 A1 discloses a biologically active dietary supplement for normalizing the androgen levels in men, improving general health and reducing obesity, said dietary supplement comprises roots and rhizomes of white cinquefoil, or aerial portions of white cinquefoil, or mixture thereof; and drone brood in the weight proportion from 20 to 80 wt %.

Another patent publication U.S. Pat. No. 5,543,146 A, discloses a dietary supplement for alleviating the symptoms associated with enlargement of the prostate gland, comprising the following ingredients: pumpkin seeds in an amount of between 12.5 to 25% by weight of the composition; Extract of Serenoa repens in an amount of between 1.875 to 18.75% by weight of the composition; Pygeum africanum in an amount of between 6.25 to 12.5% by weight of the composition; zinc glycinate in an amount of between 3.125 to 6.25% by weight of the composition; and excipients.

One of the key reasons for the reduced levels of testosterone in men is its conversion into estradiol. Aromatase is the enzyme responsible for conversion of androgens to estrogens, specifically for the conversion of testosterone into estradiol. Weight gain and aging are known to increase the loss of testosterone by this conversion. In addition, excess estradiol in men was known to be responsible for health problems related to prostate, gynocomastia and erectility/libido/hormonal balance. Aromatase inhibitors are known to increase the levels of luteinizing hormone (LH), follicle-stimulating hormone (FSH) and testosterone. Hence, the aromatase inhibitors can be used as tool to enhance the testosterone levels.

As is evident from the above, there is a continuous need in the art to provide cost-effective alternative treatments comprising highly effective herbal extracts for improving concentrations of testosterone in seminal vesicle and bloodstream. Moreover, there is a need in the art for better treatment options for improving testosterone levels that provide minimal side effects thereby making the option safe for human consumption.

OBJECT OF THE INVENTION

Therefore, the object of the present invention is to provide synergistic and safe herbal compositions comprising at least one ingredient selected from extracts, fractions, active compounds and phytochemicals or mixtures thereof derived from the plant parts of *Punica granatum* and at least one ingredient selected from extracts, fractions, active compounds and phytochemicals or mixtures thereof derived from the plant parts of *Theobroma cacao* for obtaining at least one health benefit related to enhanced anabolic and androgenic activities in the body selected from improving testosterone levels in blood stream and/or seminal vesicle, energy levels, sustained energy, vigor, stamina, healthy aging, cellular longevity, muscle mass, muscle strength sexual function (libido and erectile function) and psychological well-being (mood and focus); and alleviating the symptoms associated with the low levels of testosterone in humans such as loss of libido, loss of erectile function, abdominal obesity, decreased muscle mass and strength, decreased bone density, decreased motivation, decreased memory & concentration and improve the feelings of well-being.

Another objective of the invention is to provide use of the synergistic herbal compositions of the present invention for increasing the testosterone levels and treating/alleviating the symptoms associated with the low levels of testosterone.

Further objective of the invention is to provide methods of obtaining at least one health benefit related to enhanced anabolic and androgenic activities in the body selected from improving testosterone levels in blood stream and/or seminal vesicle, energy levels, sustained energy, vigor, stamina, healthy aging, cellular longevity, muscle mass, muscle strength sexual function (libido and erectile function) and psychological well-being (mood and focus); and alleviating the symptoms associated with the low levels of testosterone in humans such as loss of libido, erectile dysfunction, abdominal obesity, decreased muscle mass and strength, decreased bone density, decreased motivation, decreased memory & concentration and improve the feelings of well-being.

Yet another objective of the invention is to provide methods of increasing natural energy levels, physical activity, onset and increase/steady maintenance of energy, endurance, mental alertness, muscle mass and muscle strength in a mammal or warm blooded animal using the synergistic herbal compositions of the present invention.

SUMMARY OF THE INVENTION

The present invention provides synergistic herbal compositions comprising combination of a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* for obtaining at least one health benefit related to enhanced anabolic and androgenic activities in the body selected from improving testosterone levels in bloodstream and/or seminal vesicle, increasing energy levels, sustained energy, vigor, stamina, healthy aging, cellular longevity, muscle mass, muscle strength sexual function (libido and erectile function) and psychological well-being (mood and focus); reducing stress; and alleviating the symptoms associated with the low levels of testosterone in humans such as loss of libido, loss of erectile function, abdominal obesity, decreased muscle mass and strength, fatigue, mood swing, decreased bone density, decreased motivation, and decreased memory & concentration and improve the feelings of well-being.

In one aspect, the invention provides synergistic herbal compositions comprising combination of a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* for obtaining at least one health benefit related to enhanced anabolic and androgenic activities in the body selected from improving testosterone levels in bloodstream and/or seminal vesicle, energy levels, sustained energy, vigor, stamina, healthy aging, cellular longevity, muscle mass, muscle strength sexual function (libido and erectile function) and psychological well-being (mood and focus); reducing stress and alleviating the symptoms associated with the low levels of testosterone in humans, wherein the compositions contain optionally at least one additional ingredient selected from pharmaceutically acceptable excipient, pharmaceutically acceptable diluent, and pharmaceutically acceptable carrier.

The other aspect of the invention provides the use of synergistic herbal compositions comprising a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* for obtaining at least one health benefit related to enhanced anabolic and androgenic activities in the body selected from improving testosterone levels in bloodstream and/or seminal vesicle, energy levels, sustained energy, vigor, stamina, healthy aging, cellular longevity, muscle mass, muscle strength sexual function (libido and erectile function) and psychological well-being (mood and focus); and reducing stress in humans and alleviating the symptoms associated with the low levels of testosterone in humans.

Yet another aspect of the invention provides method of obtaining at least one health benefit related to enhanced anabolic and androgenic activities in the body selected from improving testosterone levels, energy levels, sustained energy, vigor, stamina healthy aging, cellular longevity, muscle mass, muscle strength sexual function (libido and erectile function) and psychological well-being (mood and focus); and reducing stress in humans; and treating/alleviating symptoms associated with low levels of testosterone such as loss of libido, erectile dysfunction, abdominal obesity, decreased muscle mass and strength, decreased bone density, decreased motivation, and decreased memory and concentration in a human wherein the method comprises supplementing humans in need thereof with an effective dose of a composition comprising a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* and optionally containing at least one additional ingredient selected from pharmaceutically acceptable excipient, pharmaceutically acceptable diluent, and pharmaceutically acceptable carrier.

Yet another aspect of the invention provides methods of increasing natural energy levels, physical activity, onset and increase/steady maintenance of energy; endurance, mental alertness, muscle mass and/or muscle strength in a mammal or warm blooded animal; wherein the method comprises supplementing the said mammal or warm blooded animal with an effective dose of a composition comprising a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* and optionally containing at least one additional ingredient selected from pharmaceutically acceptable excipient, pharmaceutically acceptable diluent, and pharmaceutically acceptable carrier.

In an additional aspect, the present invention provides synergistic herbal compositions comprising a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* and optionally combined with extracts/fractions active compound(s) and phytochemicals or mixtures of derived from the plants having the testosterone boosting activity or aromatase inhibition activity/or nitrite boosting activity.

In an additional aspect, the present invention provides synergistic herbal compositions comprising a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* and optionally combined with micronutrients such as magnesium, zinc and boron, in elemental form or compounds containing these elements; or amino acids such as D-Aspartic acid.

DESCRIPTION OF THE INVENTION

Figure 1:
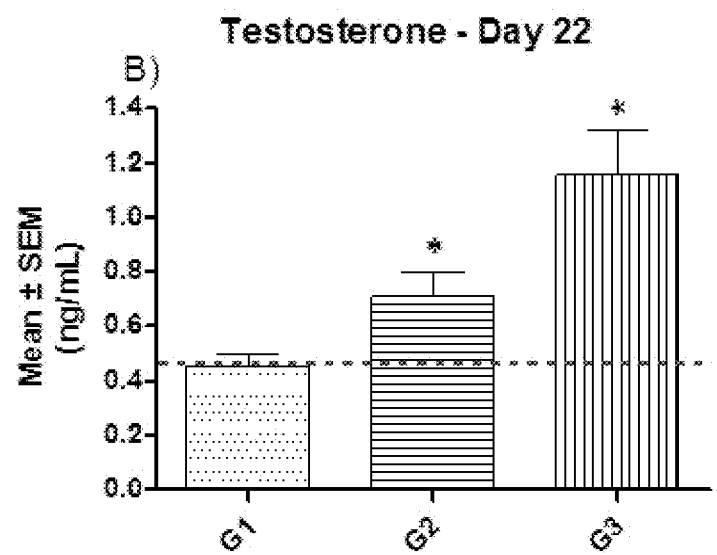
FIG. 1: The bar chart represents serum testosterone level (ng/mL) on day 22 in control group (G1) and treatment groups, G2 (composition-77: 100 mg/kg; p.o) and G3 (composition±78: 100 mg/kg; p.o); each bar represent mean±S.E.M and n=7.

Testosterone is a key androgenic male hormone and it is primarily produced by testis in Leydig cells. It is responsible for the development of male reproductive tissues and promoting secondary sexual characteristics. In adult humans, testosterone plays an important role in the maintenance of muscle mass, muscle strength, energy levels and bone mass, sexual function and psychological well-being. Increased levels of testosterone enhance muscle mass and muscle strength; increase energy levels, improves libido, erectile function and improve the feelings of well-being. The testosterone levels gradually decline as men age and the undesirable effects associated with this condition, called "andropause", have been receiving increased attention in recent years. The undesirable effects include decreased desire for sex (libido), diminished erectile quality, particularly for night time erections, changes in mood, reduced intellectual and cognitive function, fatigue, depression, and anger, decrease in muscle mass and strength, decrease in energy levels, decreased body hair, skin alterations, erectile dysfunction, abdominal obesity, decreased memory and concentration, decreased bone mass/mineral density, increase in abdominal fat mass.

Many Testosterone replacement therapies are available to treat the men suffering from testosterone deficiency but each of them has its own disadvantages. (The benefits and risks of testosterone replacement therapy: a review. Nazem Bassil, Saad Alkaade, John E Morley Ther Clin Risk Manag. 2009; 5: 427-448. Published online 2009 Jun. 22).

Hence the inventors of the current application randomly screened a large number of plant extracts and fractions for their testosterone boosting activity in an in vitro cellular model using mouse MA-10 leydig cell line and ELISA based Testosterone EIA assay kit (Cayman chemicals, USA), and found that the extracts and fractions derived from *Punica granatum* and *Theobroma cacao* show potent dose dependent testosterone boosting activities.

*Punica granatum*: *Punica granatum* Linn. (Pomegranate) is a fruit plant species of Punicaceae family locally known as Anar. It is a plant of great antiquity cultivated in the Middle East more than 5,000 years ago. The plant is found all over India and Bangladesh. In Ayurvedic medicine, the plant is described under its Sanskrit name "dalima" (fruit) as a "blood purifier" and used to cure parasitic infections, aphthae (mouth ulcers), diarrhoea, and ulcers. The fruit rind of *P. granatum* is rich in beta-carotene, potassium, phosphorous, calcium and various chemical constituents like ellagic acid, ellagitannins, punicic acid, flavonoids, anthocyanidins, anthocyanins and flavones. The potential wide-ranging therapeutic properties of Pomegranate rind or peel include treatment and prevention for cancer, cardiovascular disease, diabetes, dental conditions, and erectile dysfunction, protection from ultraviolet radiation; and as anti-diarrheal and antimicrobial. Other potential applications include infant brain ischemia, Alzheimer's disease, male infertility, arthritis, dermal wounds and obesity.

*Theobroma cacao*: *Theobroma cacao* L. is a small but economically an important tree. It is an evergreen tree of the Sterculiaceae family, native to the tropical region of the Americas. Cocao seeds are significant source of polyphenols and theobromine. The seeds are used to make cocoa mass, cocoa powder, confectionary, gouache and chocolate. The cocoa extract or its phytochemicals showed several beneficial effects against platelet aggregation, high blood pressure, atherosclerosis, hyperglycemia and hypercholesterolemia, inflammation, hepatocarcinogenesis, DNA damage and clastogenic effect.

Source of the herbs used in the invention as follows:—

1) *Punica granatum* rind raw material was collected from Kothacheruvu village, Kothacheruvu mandal, Ananthpur district, Andhra Pradesh.

2) The *Theobroma cacao* seed raw material was obtained from own cultivation in Aswaraopet, Telangana.

*Punica granatum* fruit rind was pulverized and the powder was extracted with various solvents such as ethanol, 90% aqueous ethanol, 80% aqueous ethanol, 70% aqueous ethanol, 50% aqueous ethanol, water, methanol, 50% aqueous methanol, acetone, 50% aqueous acetone and ethyl acetate to obtain ethanol extract (P.G-1), 90% aqueous ethanol extract (P.G-2), 80% aqueous ethanol extract (P.G-3), 70% aqueous ethanol extract (P.G-4), 50% aqueous ethanol extract (P.G-5), water extract (P.G-6), methanol extract (P.G-7), 50% aqueous methanol extract (P.G-8), acetone extract (P.G-9), 50% aqueous acetone extract (P.G-10) and ethyl acetate extract (P.G-11) respectively. The said extracts of *Punica granatum* fruit rind were standardized to punicalgins (I) by analytical HPLC method and the results were summarized in Table 1. Punicalgins (I) is an ellagitannin and its chemical structure is shown below.

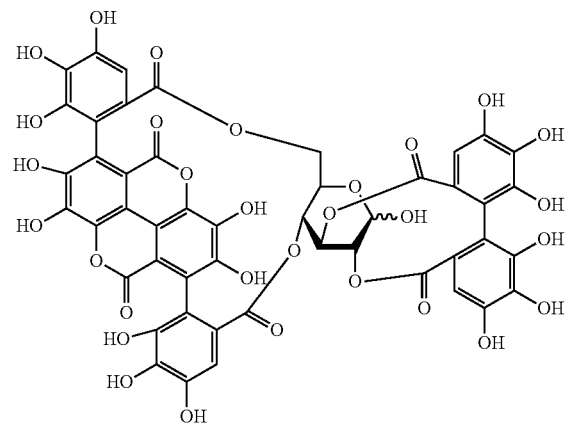

Chemical structure of punicalgins (I)

*Theobroma cacao* seed was pulverized and the powder was extracted with various solvents such as water, 50% aqueous ethanol, ethanol, 90% aqueous ethanol, 70% aqueous ethanol, methanol, 50% aqueous methanol, acetone, 50% aqueous acetone and ethyl acetate to obtain water extract (T.C-1), 50% aqueous ethanol extract (T.C-2), ethanol extract (T.C-3), 90% aqueous ethanol extract (T.C-4), 70% aqueous ethanol extract (T.C-5), methanol extract (T.C-6), 50% aqueous methanol extract (T.C-7), acetone extract (T.C-8), 50% aqueous acetone extract (T.C-9) and ethyl acetate extract (T.C-10) respectively. The said extracts of *Theobroma cacao* seed were standardized to theobromine (II) by analytical HPLC method and the results were summarized in Table 2. Theobromine (H) is the principle alkaloid in *Theobroma cacao* (Donald L. Pavia, *Journal of Chemical Education*, 1973, 50, 791-792) and its chemical structure is shown below.

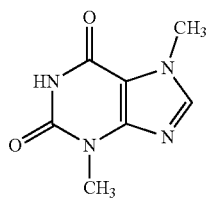

Chemical structure of theobromine (II)

The extracts of *Punica granatum* and *Theobroma cacao* potently increased testosterone levels in mouse MA-10 Leydig cells, when compared to the cells treated with control. The *Punica granatum* fruit rind 70% aq ethanol extract (P.G-4) for example at the treatment concentrations of 5 μg/mL showed 34.15% increase in testosterone over the control. Similarly, the *Theobroma cacao* seed water extract (T.C-1) and 50% aqueous ethanol extract (T.C-2) at the treatment concentration of 5 μg/mL showed 20.44% and 48.24% increase in testosterone levels respectively over the control.

The composition-1 to composition-76 were prepared by combining randomly a first ingredient selected from the extracts derived from *Punica granatum* fruit rind with a second ingredient selected from the extracts derived from seed raw material of *Theobroma cacao* at different ratios. The compositions so obtained (compositions-1 to 76) were evaluated for testosterone boosting activity in comparison with the corresponding individual ingredients. The data from in vitro testosterone assay showed that these compositions unexpectedly have better efficacy in increasing testosterone levels when compared to their corresponding individual ingredients suggesting that the individual extracts or fractions derived from *Punica granatum* have the tendency to exhibit synergism when combined with the extracts or fractions derived from *Theobroma cacao*.

For example, *Punica granatum* rind 70% aqueous ethanol extract (P.G-4) at 0.16 μg/mL and *Theobroma cacao* water extract (T.C-1) at 0.04 μg/mL showed 7.10% and 0.86% increase in testosterone concentrations respectively in cellular assay. The composition-1 containing these two extracts at 4:1 ratio showed 18.3% increase in testosterone at 0.2 μg/mL concentration, which is significantly better than the additive effect (7.10%+0.86%=7.96%) from these two ingredients, suggesting synergistic effect between *Punica granatum* rind 70% aqueous ethanol extract (P.G-4) and *Theobroma cacao* water extract (T.C-1) in enhancing the testosterone levels. The compositions-2, 3, 4, 5, 6 and 7 obtained when combining these two ingredients at ratios, 3:1, 2:1, 1:1, 1:2, 1:3 and 1:4 respectively also showed synergism, when compared to their corresponding individual ingredients as summarized in Table 3.

In the another example, *Punica granatum* rind 70% aqueous ethanol extract (P.G-4) at 0.16 μg/mL and *Theobroma cacao* 50% aqueous ethanol extract (T.C-2) at 0.04 μg/mL concentrations showed 7.10% and 3.85% increase in testosterone concentrations respectively in cellular assay. The composition-8 containing these two extracts at 4:1 ratio showed 25.74% increase in testosterone at 0.2 μg/mL concentration, which is significantly better than the additive effect (7.10%+3.85%=10.95%) from these two ingredients, suggesting synergistic effect in enhancing the testosterone levels by *Punica granatum* rind 70% aqueous ethanol extract (P.G-4) and *Theobroma cacao* 50% aqueous ethanol extract (T.C-2). These two ingredients also showed synergism when combined at ratios 3:1, 2:1, 1:1, 1:2, 1:3 and 1:4 as shown by the superior testosterone enhancing effects exhibited by the compositions-9, 10, 11, 12, 13 and 14 respectively as summarized in Table 4. Similarly compositions (C-15 to C-76) containing other extracts of *Punica granatum* and *Theobroma cacao* were also tested for testosterone boosting activity and they are found to be synergistic as summarized in Tables 5 to 8.

Testosterone Boosting Through Aromatase Inhibition

The key reasons for low levels of testosterone include disorders of pituitary and hypothalamus glands, mental and physical stress, aging, medications, concurrent illness etc. More than normal levels of testosterone is required for increasing the sexual drive, libido, enhancing muscle strength and muscle mass. The other key reason for the reduced levels of testosterone in men is its conversion to estradiol. Aromatase is the enzyme responsible for the conversion of androgens to estrogens, specifically for the conversion of testosterone into estradiol. Hence, the aromatase inhibitors can be used as a tool to inhibit the conversion of testosterone, thereby enhancing its levels in biological systems. Supplementation of aromatase inhibitors is known to increase the levels of LH, follicle-stimulating hormone (FSH) and testosterone.

Hence, the inventors of the current application screened the extracts of *Punica granatum* rind and *Theobroma cacao* seed for their aromatase inhibition activity. Interestingly, the extracts derived from both the plants materials showed potent dose dependent aromatase inhibition activity. *Punica granatum* rind 70% aq ethanol extract (P.G-4) for example at the treatment concentrations of 25 μg/mL showed 40.15% aromatase inhibitions. Similarly, *Theobroma cacao* seed 50% aq ethanol extract (T.C-2) at the treatment concentration of 25 μg/mL showed 20.9% aromatase inhibition. Therefore, it is evident that the extracts/fractions of *Punica granatum* rind and *Theobroma cacao* can have the potential to improve the levels of testosterone by inhibiting the aromatase.

Then the compositions-1 to 76 (C-1 to C-76) containing two extracts, each derived from *Punica granatum* or *Theobroma cacao*, were evaluated to explore the feasibility of obtaining synergistic efficacy in inhibiting the aromatase enzyme activity. The data from in vitro aromatase assay for these compositions unexpectedly showed better efficacy in inhibiting the aromatase enzyme activity when compared to their corresponding individual ingredients.

For example, *Punica granatum* rind 70% aqueous ethanol extract (P.G-4) at 20.0 μg/mL and *Theobroma cacao* 50% aqueous ethanol extract (T.C-2) at 5.0 μg/mL showed 22.15% and 4.18% aromatase inhibition respectively in cellular assay. The composition-8 containing these two extracts at 4:1 ratio showed 35.2% aromatase inhibition at 25.0 μg/mL concentration, which is significantly better than the additive effect (22.15%+4.18%=26.33%) from these two ingredients, suggesting synergistic effect in inhibiting the aromatase enzyme activity by *Punica granatum* rind 70% aqueous ethanol extract (P.G-4) and *Theobroma cacao* 50% aqueous ethanol extract (T.C-2). These two ingredients also showed synergistic aromatase inhibition when combined at ratios, 3:1, 2:1, 1:1, 1:2, 1:3 and 1:4 to obtain compositions 9, 10, 11, 12, 13 and 14 respectively, when compared to their corresponding individual ingredients as summarized in Table 9. Similarly other compositions containing the extracts of *Punica granatum* and *Theobroma cacao* (C-15 to C-76) were tested for aromatase inhibitory activity and the synergistic results are summarized in Tables 10 to 13.

Enhancing Physical Performance, Energy Levels, Muscle Mass and Muscle Strength

The presence and sustenance of energy is the basic requirement and condition behind all activities of human life. ATP is responsible for supplying chemical energy for numerous cellular functions including cellular transport, production of biological molecules and functioning of macromolecules, which are essential for the existence and survival of the cell. It provides energy to heart muscle (for blood circulation) and skeletal muscle (for muscle contractions needed for gross body movement). The pool of ATP that is already present in the muscle cells is good for the first 5 or 6 seconds of intense physical action, such as running, muscular activity. Beyond this time, new ATP is produced mostly through anaerobic process (glycolysis) and aerobic metabolism (cellular respiration through glycolysis, the citric acid cycle, and electron transport/oxidative phosphorylation). Overall, ATP enables the activation of muscular contractions that are needed to support longer and more vigorous physical activities. Therefore, it is essential to increase the intracellular energy source or ATP content during endurance exercise and for longer and intense period of physical activities.

Mitochondria are the site of energy production (ATP) in cells through oxidative phosphorylation, which are often called as the power-house of the cells. Mitochondria provide the majority of the total ATP required to maintain normal cellular function and homeostasis. ATP also plays a key role in skeletal muscle function as force generator for locomotion. Mitochondrial biogenesis is the process by which new mitochondria are formed in the cell through proliferation of pre-existing mitochondria. Mitochondrial biogenesis is accompanied not only by increase in number, but also in size and mass. Mitochondrial biogenesis can be induced by physical activities and pharmacological interventions including herbal ingredients. PGC-1α [PPAR (peroxisome proliferator-activated receptor)-γ coactivator-1α] is a major regulator of mitochondrial biogenesis.

Mitochondria provide most of the energy in the form of ATP for muscle cells during aerobic exercise or other physical activities. Hence, mitochondrial biogenesis, which generates more and better-functioning mitochondria can have a positive effect on increasing the level of energy and sustained energy in cells. Mitochondria are susceptible to damage and loss with aging as they are the major bioenergetic machinery and source of oxidative stress in cells. In addition, the capacity for mitochondrial biogenesis has also been shown to decrease with age. As such, effective control of mitochondrial biogenesis is critical not only for the maintenance of energy production but also for the promotion of healthy aging. Hence, the plant extracts that can induce mitochondrial biogenesis (proliferation, size and mass) can have the potential to enhance the energy, sustained energy, endurance, muscle mass, muscle strength and muscle building; and promote healthy aging.

Protein is the primary building block of muscles, bones and cartilage; and is essential for muscle growth and repair. Proteins are synthesized in the cells through translation process of mRNA utilizing amino acids. Therefore, stimulation of muscle protein synthesis is an important factor for increasing muscle mass. mTOR (mammalian target of rapamycin), a serine/threonine-protein kinase, is a central regulator of protein synthesis. Activated mTOR up-regulates protein synthesis by phosphorylating key regulators of mRNA translation and ribosome synthesis. In addition, mTOR activation increases the production of muscle specific transcription factors like MyoD and Myogenin. Hence, plant extracts or dietary supplements, which activate mTOR signaling can have the potential to enhance the muscle development, muscle mass, muscle strength and endurance.

Based on the above information, we hypothesized that the herbal extracts, fractions or their compositions/formulations which can activate protein synthesis/mTOR signaling and mitochondrial biogenesis in skeletal muscle cells would be ideally promising for increasing energy, sustained energy, endurance level, muscle tissue mass and muscle strength. Hence, the inventors of the current application randomly screened a large number of plant extracts for m-TOR and mitochondrial biogenesis activities.

Mitochondrial biogenesis assay was performed by using an in-cell ELISA kit in rat skeletal muscle (L6) cells. The extracts derived from *Punica granatum* rind and *Theobroma cacao* seed dose dependently increased mitochondrial biogenesis. *Punica granatum* rind 70% aq ethanol extract (P.G-4) for example at the treatment concentrations of 10 ng/mL dose showed 5.17% increase in mitochondrial biogenesis. Similarly, *Theobroma cacao* seed water extract (T.C-1) and 50% aq ethanol extract (T.C-2) at the treatment concentration of 10 ng/mL showed 6.04% and 9.54% increase in mitochondrial biogenesis respectively.

Selected compositions C-1 to C-7, C8, C9, C-11, C-13, C-16 and C-17 containing the extracts derived from *Punica granatum* rind and *Theobroma cacao* seed were evaluated in comparison with the corresponding individual extracts and found that the compositions exhibit synergistic efficacy as summarized in Table 14.

The individual extracts and compositions were also evaluated using mTOR phosphorylation assay in Rat L6 myoblasts. The band intensities of phospho-mTOR and mTOR protein bands in Western Blot were calculated. The relative indices (arbitrary values) obtained by phospho-mTOR/mTOR ratio indicated the extent of phosphorylation of mTOR or activation of mTOR for each treatment condition compared to the vehicle control (no treatment). The data manifests that the extracts derived from *Punica granatum* rind and *Theobroma cacao* seed and their compositions have potential to activate mTOR as summarized in table 15.

Testosterone boosting activity of selected compositions in Sprague Dawley rats: A few selected compositions of the current invention, viz Composition-77 (C-77) containing *Punica granatum* rind 70% ethanol extract (PG-4) and *Theobroma cacao* seed water extract (T.C-1) along with Ultrasperse A, microcrystalline cellulose and syloid as excipients and Composition-78 (C-78) containing *Punica granatum* rind 70% ethanol extract (PG-4) and *Theobroma cacao* seed 50% aqueous ethanol extract (T.C-2) along with maltodextrin and syloid as excipients, were evaluated for their efficacy in vivo to increase testosterone levels in male rats. Briefly, healthy male Sprague Dawley rats were acclimatized and randomized into three groups (G1 to G3). The treatment group animals were supplemented with C-77 (G2; 100 mg/kg) or C-78 (G3; 100 mg/kg; p.o.) once daily for 3 weeks in 0.5% CMC in water. The control group (G1) animals were supplemented with vehicle (0.5% CMC in water) only.

Figure 2:
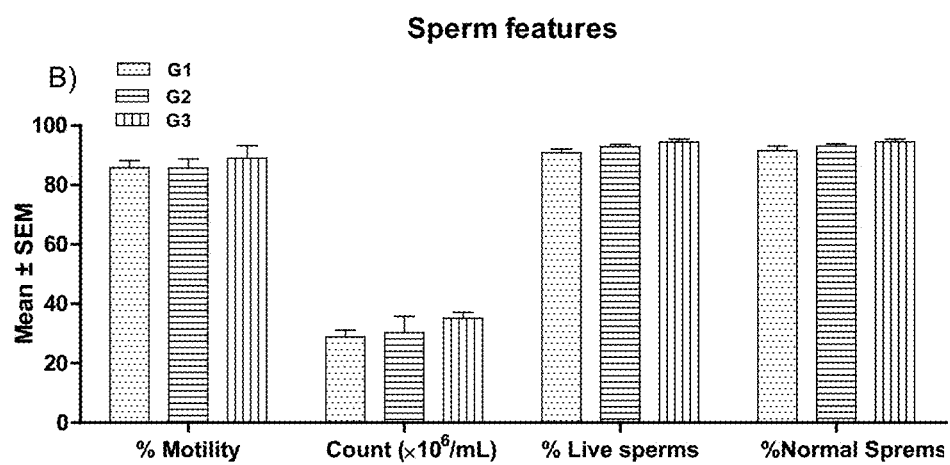
FIG. 2: The bar chart represents sperm count on day 22 in control group (G1) and treatment groups, G2 (composition-77: 100 mg/kg; p.o) and G3 (composition-78: 100 mg/kg; p.o); each bar represent mean±S.E.M, n=7. Data was analyzed using ANOVA followed by Dunnett's post-hoc test. *P<0.05, ***P<0.001 vs Normal control.

On day $22^{nd}$ blood samples were collected from all animals; sera were separated and analyzed for testosterone levels using commercially available enzyme-immunoassay kit. On day 22, the animals were euthanized, caudal epididymides along with vast deferens (both sides) were dissected out, and the semen samples were squeezed out into Dulbecco's Phosphate Buffered Saline for semen analysis. The semen analysis included, total sperm count, percent of live sperm, motile sperm and the sperm cells with normal morphology, The rats supplemented with composition-77 (G2) and composition-78 (G3) showed significantly (<0.05) increased serum testosterone levels on day 22 with 57% and 155% improvement respectively over the control group (G1). The serum testosterone levels in different treatment groups are summarized in Table 16 and depicted in FIG. 1. Similarly, the treatment groups also showed improved semen parameters, when compared to the control group as summarized in Table 17 and depicted in FIG. 2. These observations clearly suggest that the inventive compositions C-77 and C-78 increased the androgenic activity and the testicular functions in the experimental rats.

The foregoing thus demonstrates that the synergistic herbal compositions of the current invention comprising combination of a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* have the potential to improve testosterone levels, energy levels, sustained energy, vigor, healthy aging, cellular longevity, muscle mass, muscle strength, sexual function (libido and erectile function) and psychological well-being (mood and focus); and reducing stress in humans and alleviating the symptoms associated with the low levels of testosterone in humans such as loss of libido, erectile dysfunction, abdominal obesity, decreased muscle mass and strength, decreased bone density, decreased motivation, and decreased memory and concentration.

Therefore, in an important embodiment, the present invention provides synergistic herbal compositions comprising combination of a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* for obtaining at least one health benefit related to enhanced anabolic and androgenic activities in the body selected from improving testosterone levels, energy levels, sustained energy, vigor, stamina, healthy aging, cellular longevity, muscle mass, muscle strength sexual function (libido and erectile function) and psychological well-being (mood and focus); and reducing stress in humans and alleviating the symptoms associated with the low levels of testosterone in humans such as loss of libido, loss of erectile function, abdominal obesity, decreased muscle mass and strength, fatigue, mood swing, decreased bone density, decreased motivation, and decreased memory and concentration.

In other important embodiment, the present invention provides synergistic herbal compositions comprising combination of a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* and optionally containing at least one additional component selected from the group consisting of biological agent(s); pharmaceutically acceptable active ingredients, vitamins, minerals; pharmaceutically or nutraceutically or dietically acceptable, excipients, carriers or diluents for obtaining at least one health benefit related to enhanced anabolic and androgenic activities in the body selected from improving testosterone levels, energy levels, sustained energy, vigor, stamina, healthy aging, cellular longevity, muscle mass, muscle strength sexual function (libido and erectile function) and psychological well-being (mood and focus); and reducing stress in humans and alleviating the symptoms associated with the low levels of testosterone in humans such as loss of libido, loss of erectile function, abdominal obesity, decreased muscle mass and strength, fatigue, mood swing, decreased bone density, decreased motivation, and decreased memory and concentration.

In another embodiment, the invention provides the composition(s) as described above for obtaining at least one health benefit related to enhanced anabolic and androgenic activities in the body selected from improving testosterone levels, energy levels, sustained energy, vigor, stamina, healthy aging, cellular longevity, muscle mass, muscle strength sexual function (libido and erectile function) and psychological well-being (mood and focus); and reducing stress in humans and alleviating the symptoms associated with the low levels of testosterone in humans such as loss of libido, loss of erectile function, abdominal obesity, decreased muscle mass and strength, fatigue, mood swing, decreased bone density, decreased motivation, and decreased memory and concentration, wherein solvents used for preparing the extracts and fractions used in the compositions can be selected from but not limited to C1-C5 alcohols, like ethanol, methanol, n-propanol, isopropyl alcohol; ketones like acetone, methylisobutyl ketone, chlorinated solvents like methylene dichloride and chloroform, water and mixtures thereof, C1-C7 hydrocarbons such as hexane; esters like ethyl acetate and the like and mixtures thereof.

In another embodiment, the invention provides the composition(s) as described above, wherein the synergistic compositions contain optionally at least one additional component selected from the group consisting of biological agent(s); pharmaceutically active ingredients, vitamins, minerals; pharmaceutically or nutraceutically or dietically acceptable, excipients, carriers or diluents.

In another embodiment, the invention provides the composition(s) as described above for obtaining at least one health benefit related to enhanced anabolic and androgenic activities in the body selected from improving testosterone levels, energy levels, sustained energy, vigor, stamina, healthy aging, cellular longevity, muscle mass, muscle strength, sexual function (libido and erectile function) and psychological well-being (mood and focus); and reducing stress in humans and alleviating the symptoms associated with the low levels of testosterone in humans such as loss of libido, loss of erectile function, abdominal obesity, decreased muscle mass and strength, fatigue, mood swing, decreased bone density, decreased motivation, and decreased memory and concentration, wherein the plant parts used for preparing the extracts can be selected from leaves, stems, tender stems, tender twigs, aerial parts, whole fruit, fruit rind, seed, flower heads, root, bark, hardwood or whole plant or mixtures thereof.

In the other embodiment the present invention provides composition(s) as described above for obtaining at least one health benefit related to enhanced anabolic and androgenic activities in the body selected from improving testosterone levels, energy levels, sustained energy, vigor, stamina, healthy aging, cellular longevity, muscle mass, muscle strength sexual function (libido and erectile function) and psychological well-being (mood and focus); and reducing stress in humans and alleviating the symptoms associated with the low levels of testosterone in humans such as loss of libido, loss of erectile function, abdominal obesity, decreased muscle mass and strength, fatigue, mood swing, decreased bone density, decreased motivation, and decreased memory and concentration, where in the extracts or fractions are standardized to atleast one phytochemical reference marker compound or biological active marker in the extract or fraction.

In a further embodiment, the present invention provides methods of obtaining atleast one health benefit related to enhanced anabolic and androgenic activities in the body selected from improving testosterone levels, energy levels, sustained energy, vigor, stamina, healthy aging, cellular longevity, muscle mass, muscle strength sexual function (libido and erectile function) and psychological well-being (mood and focus); and reducing stress; and alleviating the symptoms associated with the low levels of testosterone such as loss of libido, loss of erectile function, abdominal obesity, decreased muscle mass and strength, fatigue, mood swing, decreased bone density, decreased motivation, and decreased memory and concentration in humans, wherein the method comprises supplementing the said human subject with an effective dose of a synergistic herbal compositions comprising combination of a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao*.

In a further embodiment, the present invention provides methods of obtaining at least one health benefit related to enhanced anabolic and androgenic activities in the body selected from improving testosterone levels, energy levels, sustained energy, vigor, stamina, healthy aging, cellular longevity, muscle mass, muscle strength, sexual function (libido and erectile function) and psychological well-being (mood and focus); and reducing stress; and alleviating the symptoms associated with the low levels of testosterone such as loss of libido, loss of erectile function, abdominal obesity, decreased muscle mass and strength, fatigue, mood swing, decreased bone density, decreased motivation, and decreased memory and concentration in a mammal or warm blooded animal, wherein the method comprises supplementing or treating the said mammal or warm blooded animal with a therapeutically effective amount of a synergistic herbal compositions comprising combination of a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* and optionally containing at least one additional ingredient selected from pharmaceutically acceptable excipient, pharmaceutically acceptable diluent, and pharmaceutically acceptable carrier.

In another exemplary embodiment the inventive synergistic herbal compositions comprising combination of a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* can further be combined optionally with biological agents and one or more pharmaceutically or dietetically acceptable excipients, carriers and diluents selected from monosaccharide's such as glucose, dextrose, fructose, galactose etc.; Disaccharides such as but not limited to sucrose, maltose, lactose, lactulose, trehalose cellobiose, chitobiose etc.; Polycarbohydrates such as Starch and modified starch such as Sodium starch glycolate, pre gelatinized starch, soluble starch, and other modified starches such as but not limited to Ultrasperse A & Ultra-tex 4; Dextrins that are produced by hydrolysis of starch or glycogen such as yellow dextrin, white dextrin, Maltodextrin etc.; Polyhydric alcohols or sugar alcohols such as but not limited to Sorbitol, mannitol, inositol, xylitol, isomalt etc.; cellulose based derivatives such as but not limited to microcrystalline cellulose, hydroxy propyl methyl cellulose, hydroxy ethyl cellulose etc.; silicates such as but not limited to neusilin, veegum, Talc, colloidal silicon dioxide etc.; metallic stearates such as but not limited to calcium stearate, magnesium stearate, zinc Stearate etc.; Organic acids such as citric acid, tartaric acid, malic acid, succinic acid, lactic acid, L-ascorbic acid etc.; Fatty acid esters and esters of poly sorbate, natural gums such as but not limited to acacia, carrageenan, Guar gum, Xanthan gum etc.; vitamin B group, nicotinamide, calcium pantothenate, amino acids, proteins such as but not limited to casein, gelatin, pectin, agar; organic metal salts such as but not limited to sodium chloride, calcium chloride, dicalcium phosphate, zinc Sulphate, zinc chloride etc.; Natural pigments, flavors, Class I & Class II preservatives and aqueous, alcoholic, hydro-alcoholic, organic solutions of above listed ingredients alone or in combination.

In another embodiment, the composition(s) of the present invention may be formulated into a dosage form selected from dry powder form, liquid form, beverage, food product, dietary supplement or any suitable form such as tablet, a capsule or a soft chewable or gummy bear.

In another embodiment of the invention, the composition(s) as disclosed above can be formulated into nutritional/dietary supplements that can be contemplated/made into the dosage form of healthy foods, or food for specified health uses such as solid food like chocolate or nutritional bars, semisolid food like cream or jam, or gel and also beverage and the like, such as refreshing beverage, instant beverage, functional beverages for sports athletes, exercising and muscle building for individuals, lactic acid bacteria beverage, drop, candy, chewing gum, gummy candy, yoghurt, ice cream, pudding, soft adzuki bean jelly, jelly, cookie, tea, soft drink, juice, milk, coffee, cereal, snack bar and the like.

In yet another embodiment, the present invention provides synergistic herbal compositions comprising combination of a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao*, where in the weight of the first ingredient varies in the range of 10%-90% and the weight of the second ingredient varies in the range of 90%-10% in the composition.

In yet another embodiment, the present invention provides synergistic herbal compositions, wherein the composition is standardized to Punicalagins in the concentration range of 0.1% to 20% by weight of the composition and theobromine in the concentration range of 0.1% to 10% by weight of the composition.

In an additional aspect, the synergistic herbal compositions of the present invention comprising combination of a first ingredient selected from the extract(s), fraction(s), active compound(s) and phytochemicals or mixtures thereof derived from the plant parts of *Punica granatum* and a second ingredient selected from the extract(s), fraction(s), active compound(s) and phytochemicals or mixtures thereof derived from the plant parts of *Theobroma cacao* can be optionally combined with micronutrients such as magnesium, zinc and boron, in elemental form or compounds containing these elements; or amino acids such as D-Aspartic acid.

In another embodiment the composition(s) of the present invention can be delivered in the form of controlled release tablets, using controlled release polymer-based coatings by the techniques including nanotechnology, microencapsulation, colloidal carrier systems and other drug delivery systems for obtaining the desired therapeutic benefit.

Those of ordinary skilled in the art will appreciate that changes could be made to the embodiments described above without departing from the broad inventive concept thereof. It is understood, therefore, that this invention is not limited to the particular embodiments or examples disclosed herein, but is intended to cover modifications within the objectives and scope of the present invention as defined in the specification. The presented examples illustrate the invention, but they should not be considered to limit the scope of the invention in any way.

EXAMPLES

Example 1: Preparation of *Punica granatum* Ethanol and Aqueous Ethanol Extracts

*Punica granatum* fruit rind (100 g) was pulverized and the powder was extracted with ethanol (700 mL) at RT for 1 h. The extract was filtered and the spent raw material was re-extracted twice with ethanol (2×500 mL) under similar conditions. The combined extract was filtered and concentrated under vacuum to obtain a residue of ethanol extract (P.G-1; 17.5 g).

The 90% aqueous ethanol extract (P.G-2; 16.5 g), 80% aqueous ethanol extract (P.G-3; 27.0 g), 70% aqueous ethanol extract (P.G-4; 35.7 g) and 50% aqueous ethanol extract (P.G-5; 38.0 g) of *Punica granatum* fruit rind were obtained by adopting similar extraction procedure as described above using 90% aqueous ethanol, 80% aqueous ethanol, 70% aqueous ethanol and 50% aqueous ethanol as extraction solvents respectively.

Example 2: Preparation of *Punica granatum* Water Extract

*Punica granatum* fruit rind (100 g) was pulverized and the powder was extracted with water (700 mL) at RT for 1 h. The extract was filtered and the spent raw material was re-extracted twice with water (2×500 mL) under similar conditions. The combined extract was filtered and concentrated under vacuum to obtain a residue of water extract (P.G-6; 38.5 g).

Example 3: Preparation of *Punica granatum* Methanol and Aqueous Methanol Extracts

*Punica granatum* fruit rind (100 g) was pulverized and the powder was extracted with methanol (700 mL) at RT for 1 h. The extract was filtered and the spent raw material was re-extracted twice with methanol (2×500 mL) under similar conditions. The combined extract was filtered and concentrated under vacuum to obtain a residue of methanol extract (P.G-7; 25.0 g).

The 50% aqueous methanol extract (P.G-8; 34.4 g) of *Punica granatum* fruit rind was obtained by adopting similar procedure using 50% aqueous methanol as extraction solvent.

Example 4: Preparation of *Punica granatum* Acetone and Aqueous Acetone Extracts

*Punica granatum* fruit rind (100 g) was pulverized and the powder was extracted with acetone (700 mL) at RT for 1 h. The extract was filtered and the spent raw material was re-extracted twice with acetone (2×500 mL) under similar conditions. The combined extract was filtered and concentrated under vacuum to obtain a residue of acetone extract (P.G-9; 4.2 g).

The 50% aqueous acetone extract (P.G-10; 47.6 g) of *Punica granatum* fruit rind was obtained by adopting similar procedure using 50% aqueous acetone as extraction solvent.

Example 5: Preparation of *Punica granatum* Ethyl Acetate Extract

*Punica granatum* fruit rind (100 g) was pulverized and the powder was extracted with ethyl acetate (700 mL) at RT for 1 h. The extract was filtered and the spent raw material was re-extracted twice with ethyl acetate (2×500 mL) under similar conditions. The combined extract was filtered and concentrated under vacuum to obtain a residue of ethyl acetate extract (P.G-11; 1.1 g).

Example 6: Standardization of *Punica granatum* Extracts

The various extracts of *Punica granatum* were standardized to punicalagin by analytical HPLC method and the results were summarized in Table 1.

TABLE 1

| S. No. | Extract code | Solvent for extraction | Weight of the product | Punicalagins (HPLC) |
|---|---|---|---|---|
| 1 | P.G-1 | Ethanol | 17.5 g | 8.05% |
| 2 | P.G-2 | 90% ethanol | 16.5 g | 13.86% |
| 3 | P.G-3 | 80% ethanol | 27.0 g | 14.6% |
| 4 | P.G-4 | 70% ethanol | 35.7 g | 13.4% |
| 5 | P.G-5 | 50% ethanol | 38.0 g | 9.5% |
| 6 | P.G-6 | water | 38.5 g | 2.5% |
| 7 | P.G-7 | Methanol | 25.0 g | 11.6% |
| 8 | P.G-8 | 50% methanol | 34.4 g | 8.9% |
| 9 | P.G-9 | Acetone | 4.2 g | 15.4% |
| 10 | P.G-10 | 50% acetone | 47.6 g | 12.14% |
| 11 | P.G-11 | Ethyl acetate | 1.1 g | 0.43% |

Example 7: Preparation of *Theobroma cacao* Seed Water Extract

*Theobroma cacao* seeds (100 g) were pulverized and the powder was extracted with water (700 mL) at RT for 1 h. The extract was filtered and the spent raw material was re-extracted twice with water (2×500 mL) under similar conditions. The combined extract was filtered and concentrated under vacuum to obtain a residue of water extract as a powder (T.C-1; 11.3 g).

Example 8: Preparation of *Theobroma cacao* Seed Ethanol and Aqueous Ethanol Extracts

*Theobroma cacao* seeds (100 g) were pulverized and the powder was extracted with 50% aqueous ethanol (700 mL)

at RT for 1 h. The extract was filtered and the spent raw material was re-extracted twice with 50% aqueous ethanol (2×500 mL) under similar conditions. The combined extract was filtered and concentrated under vacuum to obtain a residue of 50% aqueous ethanol extract (T.C-2; 9.9 g).

The ethanol extract (T.C-3; 4.4 g), 90% aqueous ethanol extract (T.C-4; 4.5 g) and 70% aqueous ethanol extract (T.C-5; 8.3 g) of *Theobroma cacao* seeds were obtained by adopting similar extraction procedure using ethanol, 90% aqueous ethanol and 70% aqueous ethanol as extraction solvents respectively.

Example 9: Preparation of *Theobroma cacao* Seed Methanol and Aqueous Methanol Extracts

*Theobroma cacao* seeds (100 g) were pulverized and the powder was extracted with methanol (700 mL) at RT for 1 h. The extract was filtered and the spent raw material was re-extracted twice with methanol (2×500 mL) under similar conditions. The combined extract was filtered and concentrated under vacuum to obtain a residue of methanol extract (T.C-6; 5.8 g).

The 50% aqueous methanol extract (T.C-7; 10.0 g) of *Theobroma cacao* seeds were obtained by adopting similar procedure using 50% methanol as extraction solvent.

Example 10: Preparation of *Theobroma cacao* Seed Acetone and Aqueous Acetone Extracts

*Theobroma cacao* seeds (100 g) were pulverized and the powder was extracted with acetone (700 mL) at RT for 1 h. The extract was filtered and the spent raw material was re-extracted twice with acetone (2×500 mL) under similar conditions. The combined extract was filtered and concentrated under vacuum to obtain a residue of acetone extract (T.C-8; 27.5 g).

The 50% aqueous acetone extract (T.C-9; 13.5 g) of *Theobroma cacao* seeds were obtained by adopting similar procedure using 50% acetone as extraction solvent.

Example 11: Preparation of *Theobroma cacao* Seed Ethyl Acetate Extract

*Theobroma cacao* seeds (100 g) were pulverized and the powder was extracted with ethyl acetate (700 mL) at RT for 1 h. The extract was filtered and the spent raw material was re-extracted twice with ethyl acetate (2×500 mL) under similar conditions. The combined extract was filtered and concentrated under vacuum to obtain ethyl acetate extract (T.C-10; 28.5 g).

Example 12: Standardization of *Theobroma cacao* Seed Extracts

The various extracts of *Theobroma cacao* seed were standardized to Theobromine by analytical HPLC method and the results were summarized in Table 2.

TABLE 2

| S. No. | Extract code | Solvent for extraction | Weight of the product | Theobromine (HPLC) |
|---|---|---|---|---|
| 1 | T.C-1 | water | 11.3 g | 3.69% |
| 2 | T.C-2 | 50% ethanol | 9.9 g | 6.8% |
| 3 | T.C-3 | Ethanol | 4.4 g | 7.5% |
| 4 | T.C-4 | 90% ethanol | 4.5 g | 9.2% |
| 5 | T.C-5 | 70% ethanol | 8.3 g | 7.7% |
| 6 | T.C-6 | Methanol | 5.8 g | 5.99% |
| 7 | T.C-7 | 50% methanol | 10.0 g | 6.9% |
| 8 | T.C-8 | Acetone | 27.5 g | 0.79% |
| 9 | T.C-9 | 50% acetone | 13.5 g | 7.26% |
| 10 | T.C-10 | Ethyl acetate | 28.5 g | 0.35% |

Example 13: Preparation of Compositions Containing *Punica granatum* Peel 70% Aqueous Ethanol Extract and *Theobroma cacao* Seed Water Extract Composition-1 (C-1): The composition-1 was prepared by combining *Punica granatum* 70% aqueous ethanol extract (P.G-4) and *Theobroma cacao* water extract (T.C-1) in the ratio of 4:1.

Composition-2 (C-2): The composition-2 was prepared by combining *Punica granatum* 70% aqueous ethanol extract (P.G-4) and *Theobroma cacao* water extract (T.C-1) in the ratio of 3:1.

Composition-3 (C-3): The composition-3 was prepared by combining *Punica granatum* 70% aqueous ethanol extract (P.G-4) and *Theobroma cacao* water extract (T.C-1) in the ratio of 2:1.

Composition-4 (C-4): The composition-4 was prepared by combining *Punica granatum* 70% aqueous ethanol extract (P.G-4) and *Theobroma cacao* water extract (T.C-1) in the ratio of 1:1.

Composition-5 (C-5): The composition-5 was prepared by combining *Punica granatum* 70% aqueous ethanol extract (P.G-4) and *Theobroma cacao* water extract (T.C-1) in the ratio of 1:2.

Composition-6 (C-6): The composition-6 was prepared by combining *Punica granatum* 70% aqueous ethanol extract (P.G-4) and *Theobroma cacao* water extract (T.C-1) in the ratio of 1:3.

Composition-7 (C-7): The composition-7 was prepared by combining *Punica granatum* 70% ethanol extract (P.G-4) and *Theobroma cacao* water extract (T.C-1) in the ratio of 1:4.

Example 14: Preparation of Compositions Containing *Punica granatum* Peel 70% Aqueous Ethanol Extract and *Theobroma cacao* Seed 50% Aqueous Ethanol Extract Composition-8 (C-8): The composition-8 was prepared by combining *Punica granatum* 70% aqueous ethanol extract (P.G-4) and *Theobroma cacao* 50% aqueous ethanol extract (T.C-2) in the ratio of 4:1.

Composition-9 (C-9): The composition-9 was prepared by combining *Punica granatum* 70% aqueous ethanol extract (P.G-4) and *Theobroma cacao* 50% aqueous ethanol extract (T.C-2) in the ratio of 3:1.

Composition-10 (C-10): The composition-10 was prepared by combining *Punica granatum* 70% aqueous ethanol extract (P.G-4) and *Theobroma cacao* 50% aqueous ethanol extract (T.C-2) in the ratio of 2:1.

Composition-li (C-11): The composition-11 was prepared by combining *Punica granatum* 70% aqueous ethanol extract (P.G-4) and *Theobroma cacao* 50% aqueous ethanol extract (T.C-2) in the ratio of 1:1.

Composition-12 (C-12): The composition-12 was prepared by combining *Punica granatum* 70% aqueous ethanol extract (P.G-4) and *Theobroma cacao* 50% aqueous ethanol extract (T.C-2) in the ratio of 1:2.

Composition-13 (C-13): The composition-13 was prepared by combining *Punica granatum* 70% aqueous ethanol extract (P.G-4) and *Theobroma cacao* 50% aqueous ethanol extract (T.C-2) in the ratio of 1:3.

Composition-14 (C-14): The composition-14 was prepared by combining *Punica granatum* 70% aqueous ethanol extract (P.G-4) and *Theobroma cacao* 50% aqueous ethanol extract (T.C-2) in the ratio of 1:4.

Example 15: Preparation of Compositions Containing *Punica granatum* Peel 70% Aqueous Ethanol Extract and *Theobroma cacao* Seed 90% Aqueous Ethanol or 70% Aqueous Ethanol Extract Composition-15 (C-15): The composition-15 was prepared by combining *Punica granatum* 70% aqueous ethanol extract (P.G-4) and *Theobroma cacao* 90% aqueous ethanol extract (T.C-4) in the ratio of 4:1.

Composition-16 (C-16): The composition-16 was prepared by combining *Punica granatum* 70% aqueous ethanol extract (P.G-4) and *Theobroma cacao* 90% aqueous ethanol extract (T.C-4) in the ratio of 3:1.

Composition-17 (C-17): The composition-17 was prepared by combining *Punica granatum* 70% aqueous ethanol extract (P.G-4) and *Theobroma cacao* 90% aqueous ethanol extract (T.C-4) in the ratio of 2:1.

Composition-18 (C-18): The composition-18 was prepared by combining *Punica granatum* 70% aqueous ethanol extract (P.G-4) and *Theobroma cacao* 90% aqueous ethanol extract (T.C-4) in the ratio of 1:1.

Composition-19 (C-19): The composition-19 was prepared by combining *Punica granatum* 70% aqueous ethanol extract (P.G-4) and *Theobroma cacao* 90% aqueous ethanol extract (T.C-4) in the ratio of 1:2.

Composition-20 (C-20): The composition-20 was prepared by combining *Punica granatum* 70% aqueous ethanol extract (P.G-4) and *Theobroma cacao* 90% aqueous ethanol extract (T.C-4) in the ratio of 1:3.

Composition-21 (C-21): The composition-21 was prepared by combining *Punica granatum* 70% aqueous ethanol extract (P.G-4) and *Theobroma cacao* 90% aqueous ethanol extract (T.C-4) in the ratio of 1:4.

Composition-22 (C-22): The composition-22 was prepared by combining *Punica granatum* 70% aqueous ethanol extract (P.G-4) and *Theobroma cacao* 70% aqueous ethanol extract (T.C-5) in the ratio of 4:1.

Composition-23 (C-23): The composition-23 was prepared by combining *Punica granatum* 70% aqueous ethanol extract (P.G-4) and *Theobroma cacao* 70% aqueous ethanol extract (T.C-5) in the ratio of 3:1.

Composition-24 (C-24): The composition-24 was prepared by combining *Punica granatum* 70% aqueous ethanol extract (P.G-4) and *Theobroma cacao* 70% aqueous ethanol extract (T.C-5) in the ratio of 2:1.

Composition-25 (C-25): The composition-25 was prepared by combining *Punica granatum* 70% aqueous ethanol extract (P.G-4) and *Theobroma cacao* 70% aqueous ethanol extract (T.C-5) in the ratio of 1:1.

Composition-26 (C-26): The composition-26 was prepared by combining *Punica granatum* 70% aqueous ethanol extract (P.G-4) and *Theobroma cacao* 70% aqueous ethanol extract (T.C-5) in the ratio of 1:2.

Composition-27 (C-27): The composition-27 was prepared by combining *Punica granatum* 70% aqueous ethanol extract (P.G-4) and *Theobroma cacao* 70% aqueous ethanol extract (T.C-5) in the ratio of 1:3.

Composition-28 (C-28): The composition-28 was prepared by combining *Punica granatum* 70% aqueous ethanol extract (P.G-4) and *Theobroma cacao* 70% aqueous ethanol extract (T.C-5) in the ratio of 1:4.

Example 16: Preparation of Compositions Containing *Punica granatum* Peel 70% Aqueous Ethanol Extract and *Theobroma cacao* Seed Methanol or 50% Aqueous Methanol or Acetone or 50% Aqueous Acetone or Ethyl Acetate Extract Composition-29 (C-29): The composition-29 was prepared by combining *Punica granatum* 70% aqueous ethanol extract (P.G-4) and *Theobroma cacao* methanol extract (T.C-6) in the ratio of 2:1.

Composition-30 (C-30): The composition-30 was prepared by combining *Punica granatum* 70% aqueous ethanol extract (P.G-4) and *Theobroma cacao* methanol extract (T.C-6) in the ratio of 1:1.

Composition-31 (C-31): The composition-31 was prepared by combining *Punica granatum* 70% aqueous ethanol extract (P.G-4) and *Theobroma cacao* methanol extract (T.C-6) in the ratio of 1:2.

Composition-32 (C-32): The composition-32 was prepared by combining *Punica granatum* 70% aqueous ethanol extract (P.G-4) and *Theobroma cacao* 50% methanol extract (T.C-7) in the ratio of 2:1.

Composition-33 (C-33): The composition-33 was prepared by combining *Punica granatum* 70% aqueous ethanol extract (P.G-4) and *Theobroma cacao* 50% methanol extract (T.C-7) in the ratio of 1:1.

Composition-34 (C-34): The composition-34 was prepared by combining *Punica granatum* 70% aqueous ethanol extract (P.G-4) and *Theobroma cacao* 50% methanol extract (T.C-7) in the ratio of 1:2.

Composition-35 (C-35): The composition-35 was prepared by combining *Punica granatum* 70% aqueous ethanol extract (P.G-4) and *Theobroma cacao* acetone extract (T.C-8) in the ratio of 2:1.

Composition-36 (C-36): The composition-36 was prepared by combining *Punica granatum* 70% aqueous ethanol extract (P.G-4) and *Theobroma cacao* acetone extract (T.C-8) in the ratio of 1:1.

Composition-37 (C-37): The composition-37 was prepared by combining *Punica granatum* 70% aqueous ethanol extract (P.G-4) and *Theobroma cacao* acetone extract (T.C-8) in the ratio of 1:2.

Composition-38 (C-38): The composition-38 was prepared by combining *Punica granatum* 70% aqueous ethanol extract (P.G-4) and *Theobroma cacao* 50% aqueous acetone extract (T.C-9) in the ratio of 2:1.

Composition-39 (C-39): The composition-39 was prepared by combining *Punica granatum* 70% aqueous ethanol extract (P.G-4) and *Theobroma cacao* 50% aqueous acetone extract (T.C-9) in the ratio of 1:1.

Composition-40 (C-40): The composition-40 was prepared by combining *Punica granatum* 70% aqueous ethanol extract (P.G-4) and *Theobroma cacao* 50% aqueous acetone extract (T.C-9) in the ratio of 1:2.

Composition-41 (C-41): The composition-41 was prepared by combining *Punica granatum* 70% aqueous ethanol extract (P.G-4) and *Theobroma cacao* ethyl acetate extract (T.C-10) in the ratio of 2:1.

Composition-42 (C-42): The composition-42 was prepared by combining *Punica granatum* 70% aqueous ethanol extract (P.G-4) and *Theobroma cacao* ethyl acetate extract (T.C-10) in the ratio of 1:1.

Composition-43 (C-43): The composition-43 was prepared by combining *Punica granatum* 70% aqueous ethanol extract (P.G-4) and *Theobroma cacao* ethyl acetate extract (T.C-10) in the ratio of 1:2.

Example 17: Preparation of Compositions Containing *Punica granatum* Peel Ethanol or 50% Aqueous Ethanol or Water Extract and *Theobroma cacao* Seed Ethanol or Water or 50% Aqueous Ethanol Extract Composition-44 (C-44): The composition-44 was prepared by combining *Punica granatum* ethanol extract (P.G-1) and *Theobroma cacao* ethanol extract (T.C-3) in the ratio of 2:1.

Composition-45 (C-45): The composition-45 was prepared by combining *Punica granatum* ethanol extract (P.G-1) and *Theobroma cacao* ethanol extract (T.C-3) in the ratio of 1:1.

Composition-46 (C-46): The composition-46 was prepared by combining *Punica granatum* ethanol extract (P.G-1) and *Theobroma cacao* ethanol extract (T.C-3) in the ratio of 1:2.

Composition-47 (C-47): The composition-47 was prepared by combining *Punica granatum* ethanol extract (P.G-1) and *Theobroma cacao* water extract (T.C-1) in the ratio of 2:1.

Composition-48 (C-48): The composition-48 was prepared by combining *Punica granatum* ethanol extract (P.G-1) and *Theobroma cacao* water extract (T.C-1) in the ratio of 1:1.

Composition-49 (C-49): The composition-49 was prepared by combining *Punica granatum* ethanol extract (P.G-1) and *Theobroma cacao* water extract (T.C-1) in the ratio of 1:2.

Composition-50 (C-50): The composition-50 was prepared by combining *Punica granatum* 50% aqueous ethanol extract (P.G-5) and *Theobroma cacao* ethanol extract (T.C-3) in the ratio of 2:1.

Composition-51 (C-51): The composition-51 was prepared by combining *Punica granatum* 50% aqueous ethanol extract (P.G-5) and *Theobroma cacao* ethanol extract (T.C-3) in the ratio of 1:1.

Composition-52 (C-52): The composition-52 was prepared by combining *Punica granatum* 50% aqueous ethanol extract (P.G-5) and *Theobroma cacao* ethanol extract (T.C-3) in the ratio of 1:2.

Composition-53 (C-53): The composition-53 was prepared by combining *Punica granatum* 50% aqueous ethanol extract (P.G-5) and *Theobroma cacao* water extract (T.C-1) in the ratio of 2:1.

Composition-54 (C-54): The composition-54 was prepared by combining *Punica granatum* 50% aqueous ethanol extract (P.G-5) and *Theobroma cacao* water extract (T.C-1) in the ratio of 1:1.

Composition-55 (C-55): The composition-55 was prepared by combining *Punica granatum* 50% aqueous ethanol extract (P.G-5) and *Theobroma cacao* water extract (T.C-1) in the ratio of 1:2.

Composition-56 (C-56): The composition-56 was prepared by combining *Punica granatum* water extract (P.G-6) and *Theobroma cacao* 50% aqueous ethanol extract (T.C-2) in the ratio of 2:1.

Composition-57 (C-57): The composition-57 was prepared by combining *Punica granatum* water extract (P.G-6) and *Theobroma cacao* 50% aqueous ethanol extract (T.C-2) in the ratio of 1:1.

Composition-58 (C-58): The composition-58 was prepared by combining *Punica granatum* water extract (P.G-6) and *Theobroma cacao* 50% aqueous ethanol extract (T.C-2) in the ratio of 1:2.

Composition-59 (C-59): The composition-59 was prepared by combining *Punica granatum* water extract (P.G-6) and *Theobroma cacao* water extract (T.C-1) in the ratio of 2:1.

Composition-60 (C-60): The composition-60 was prepared by combining *Punica granatum* water extract (P.G-6) and *Theobroma cacao* water extract (T.C-1) in the ratio of 1:1.

Composition-61 (C-61): The composition-61 was prepared by combining *Punica granatum* water extract (P.G-6) and *Theobroma cacao* water extract (T.C-1) in the ratio of 1:2.

Example 18: Preparation of Compositions Containing *Punica granatum* Peel Methanol or 50% Aqueous Methanol or Acetone or 50% Aqueous Acetone or Ethyl Acetate Extract and *Theobroma cacao* Seed 50% Aqueous Ethanol or Water Extract Composition-62 (C-62): The composition-62 was prepared by combining *Punica granatum* methanol extract (P.G-7) and *Theobroma cacao* 50% aqueous ethanol extract (T.C-2) in the ratio of 2:1.

Composition-63 (C-63): The composition-63 was prepared by combining *Punica granatum* methanol extract (P.G-7) and *Theobroma cacao* 50% aqueous ethanol extract (T.C-2) in the ratio of 1:1.

Composition-64 (C-64): The composition-64 was prepared by combining *Punica granatum* methanol extract (P.G-7) and *Theobroma cacao* 50% aqueous ethanol extract (T.C-2) in the ratio of 1:2.

Composition-65 (C-65): The composition-65 was prepared by combining *Punica granatum* 50% aqueous methanol extract (P.G-8) and *Theobroma cacao* water extract (T.C-1) in the ratio of 2:1.

Composition-66 (C-66): The composition-66 was prepared by combining *Punica granatum* 50% aqueous methanol extract (P.G-8) and *Theobroma cacao* water extract (T.C-1) in the ratio of 1:1.

Composition-67 (C-67): The composition-67 was prepared by combining *Punica granatum* 50% aqueous methanol extract (P.G-8) and *Theobroma cacao* water extract (T.C-1) in the ratio of 1:2.

Composition-68 (C-68): The composition-68 was prepared by combining *Punica granatum* acetone extract (P.G-9) and *Theobroma cacao* 50% aqueous ethanol extract (T.C-2) in the ratio of 2:1.

Composition-69 (C-69): The composition-69 was prepared by combining *Punica granatum* acetone extract (P.G-9) and *Theobroma cacao* 50% aqueous ethanol extract (T.C-2) in the ratio of 1:1.

Composition-70 (C-70): The composition-70 was prepared by combining *Punica granatum* acetone extract (P.G-9) and *Theobroma cacao* 50% aqueous ethanol extract (T.C-2) in the ratio of 1:2.

Composition-71 (C-71): The composition-71 was prepared by combining *Punica granatum* 50% aqueous acetone extract (P.G-10) and *Theobroma cacao* water extract (T.C-1) in the ratio of 2:1.

Composition-72 (C-72): The composition-72 was prepared by combining *Punica granatum* 50% aqueous acetone extract (P.G-10) and *Theobroma cacao* water extract (T.C-1) in the ratio of 1:1.

Composition-73 (C-73): The composition-73 was prepared by combining *Punica granatum* 50% aqueous acetone extract (P.G-10) and *Theobroma cacao* water extract (T.C-1) in the ratio of 1:2.

Composition-74 (C-74): The composition-74 was prepared by combining *Punica granatum* ethyl acetate extract (P.G-11) and *Theobroma cacao* water extract (T.C-1) in the ratio of 2:1.

Composition-75 (C-75): The composition-75 was prepared by combining *Punica granatum* ethyl acetate extract (P.G-11) and *Theobroma cacao* water extract (T.C-1) in the ratio of 1:1.

Composition-76 (C-76): The composition-76 was prepared by combining *Punica granatum* ethyl acetate extract (P.G-11) and *Theobroma cacao* water extract (T.C-1) in the ratio of 1:2.

Example 19: Formulation of the Compositions

Composition-77 (C-77): The composition-77 was prepared by combining 60 g of *Punica granatum* peel 70% aqueous ethanol extract (P.G-4), 15 g of *Theobroma cacao* water extract (T.C-1), 10 g of Ultrasperse A, 13 g of microcrystalline cellulose and 2 g of syloid in presence of ethanol/water and then drying to give the composition.

Composition-78 (C-78): The composition-78 was prepared by combining 60 g of *Punica granatum* peel 70% aqueous ethanol extract (P.G-4), 15 g of *Theobroma cacao* 50% aqueous ethanol extract (T.C-2), 23 g of maltodextrin and 2 g of syloid in presence of ethanol/water and then drying to give the composition.

Example 20: General Procedure for Testosterone Assay

The herbal extracts and their compositions were evaluated for their ability to induce testosterone production in MA-10 mouse leydig cell line (ATCC, Manassas, VA, USA). The cells were cultured in 0.1% gelatin coated flasks in presence of DMEM: F12 medium (ATCC, Manassas, VA, USA) supplemented with 15% horse serum and 20 mM HEPES at 37° C. in a C02 incubator. Equal number of cells was plated in each well of a gelatin coated 96-well cell culture plate and allowed to attach overnight. The washed cells were supplemented with serum free-DMEM: F12 medium and treated with different concentrations of the test samples and incubated further for 48 h. Culture wells receiving 0.2% DMSO was considered as vehicle control and luteinizing hormone was used as positive control. The culture supernatants were collected, clarified at 10000 g for 5 min at 4° C., and used for Testosterone estimation using a specific commercially available ELISA kit.

ELISA was performed using Testosterone EIA kit (Cayman chemicals, Ann Arbor, MI, USA) according to the manufacturer's protocol. This assay is based on competition between testosterone and a testosterone-Acetylcholinesterase (AchE) conjugate (Testosterone tracer) for a limited amount of testosterone antibody.

Ellman's reagent containing the substrate of AchE is used to detect the enzyme activity. The product of the enzyme reaction is yellow in color and absorbs strongly at 412 nm. The intensity of the color is proportional to the amount of the Testosterone tracer bound to the well and inversely proportional to the testosterone available in the test samples. Fifty microliters samples of cell free culture supernatants were used to estimate the Testosterone content. A standard curve was plotted with a set of known concentrations of testosterone standards as per protocol. The reported sensitivity of the assay kit was 6 pg/ml. The results are summarized in Table 3-8.

TABLE 3

Testosterone activity of the compositions containing *Punica granatum* peel 70% ethanol extract and *Theobroma cacao* seed water extract.

| | P.G-4 | | T.C-1 | | | Comp | % increase of testosterone over control | |
|---|---|---|---|---|---|---|---|---|
| | | | | | | | Additive | |
| Comp # | µg/mL | % increase | µg/mL | % increase | Ratio | Dose µg/mL | (Calculated) | Observed |
| C-1 | 0.16 | 7.10 | 0.04 | 0.86 | 4:1 | 0.2 | 7.96 | 18.3 |
| C-2 | 0.15 | 6.66 | 0.05 | 1.07 | 3:1 | 0.2 | 7.73 | 21.28 |
| C-3 | 0.13 | 5.77 | 0.07 | 1.50 | 2:1 | 0.2 | 7.27 | 32.55 |
| C-4 | 0.1 | 4.44 | 0.1 | 2.14 | 1:1 | 0.2 | 6.58 | 21.35 |
| C-6 | 0.25 | 3.95 | 0.75 | 2.93 | 1:3 | 1.0 | 6.88 | 12.52 |
| C-7 | 0.2 | 3.16 | 0.8 | 3.13 | 1:4 | 1.0 | 6.29 | 20.29 |

TABLE 4

Testosterone activity of the compositions containing *Punica granatum* peel 70% ethanol extract and *Theobroma cacao* seed 50% aqueous ethanol extract.

| | P.G-4 | | T.C-2 | | | Comp | % increase of testosterone over control | |
|---|---|---|---|---|---|---|---|---|
| | | | | | | | Additive | |
| Comp # | µg/mL | % increase | µg/mL | % increase | Ratio | Dose µg/mL | (Calculated) | Observed |
| C-8 | 0.16 | 7.10 | 0.04 | 3.85 | 4:1 | 0.2 | 10.95 | 25.74 |
| C-9 | 0.15 | 6.66 | 0.05 | 4.81 | 3:1 | 0.2 | 11.47 | 28.1 |
| C-10 | 0.13 | 5.77 | 0.07 | 6.74 | 2:1 | 0.2 | 12.51 | 28.1 |
| C-11 | 0.1 | 4.44 | 0.1 | 9.62 | 1:1 | 0.2 | 14.06 | 27.13 |
| C-14 | 0.04 | 3.56 | 0.16 | 15.4 | 1:4 | 0.2 | 18.96 | 23.41 |

TABLE 5

Testosterone activity of the compositions containing *Punica granatum* peel 70% ethanol extract and *Theobroma cacao* seed 90% aqueous ethanol or 70% aqueous ethanol extract.

| | P.G-4 | | T.C-4 | | | Comp | % increase of testosterone over control | |
|---|---|---|---|---|---|---|---|---|
| | | | | | | | Additive | |
| Comp # | µg/mL | % increase | µg/mL | % increase | Ratio | Dose µg/mL | (Calculated) | Observed |
| C-16 | 0.15 | 0.27 | 0.05 | 1.93 | 3:1 | 0.2 | 2.20 | 19.04 |
| C-17 | 0.67 | 6.49 | 0.33 | 3.56 | 2:1 | 1.0 | 10.05 | 22.02 |

TABLE 5-continued

Testosterone activity of the compositions containing *Punica granatum* peel 70% ethanol extract and *Theobroma cacao* seed 90% aqueous ethanol or 70% aqueous ethanol extract.

| Comp # | µg/mL | % increase | µg/mL | % increase | Ratio | Comp Dose µg/mL | Additive (Calculated) | Observed |
|---|---|---|---|---|---|---|---|---|
| C-18 | 0.5 | 4.84 | 0.5 | 5.39 | 1:1 | 1.0 | 10.23 | 18.59 |
| C-21 | 0.04 | 0.07 | 0.16 | 6.19 | 1:4 | 0.2 | 6.26 | 11.75 |
| | P.G-4 | | T.C-5 | | | | | |
| C-23 | 0.75 | 4.29 | 0.25 | 4.08 | 3:1 | 1.0 | 8.37 | 17.06 |
| C-24 | 0.67 | 3.83 | 0.33 | 5.39 | 2:1 | 1.0 | 9.22 | 24.92 |
| C-25 | 0.5 | 2.86 | 0.5 | 8.17 | 1:1 | 1.0 | 11.03 | 24.92 |

TABLE 6

Testosterone activity of the compositions containing *Punica granatum* peel 70% ethanol extract and *Theobroma cacao* seed aqueous methanol or 50% aqueous acetone or ethyl acetate extract.

| Comp # | µg/mL | % increase | µg/mL | % increase | Ratio | Comp Dose µg/mL | Additive (Calculated) | Observed |
|---|---|---|---|---|---|---|---|---|
| | P.G-4 | | T.C-7 | | | | | |
| C-34 | 0.07 | 10.13 | 0.13 | 4.42 | 1:2 | 0.2 | 14.55 | 24.09 |
| | P.G-4 | | T.C-9 | | | | | |
| C-38 | 0.13 | 15.80 | 0.07 | 8.89 | 2:1 | 0.2 | 24.69 | 30.37 |
| | P.G-4 | | T.C-10 | | | | | |
| C-41 | 0.67 | 6.09 | 0.33 | 0.81 | 2:1 | 1.0 | 6.90 | 9.52 |
| C-42 | 0.5 | 4.55 | 0.5 | 1.23 | 1:1 | 1.0 | 5.78 | 9.91 |
| C-43 | 0.33 | 3.00 | 0.67 | 1.65 | 1:2 | 1.0 | 4.65 | 10.94 |

TABLE 7

Testosterone activity of the compositions containing *Punica granatum* peel ethanol or 50% aqueous ethanol or water extract and *Theobroma cacao* seed ethanol or water or 50% aqueous ethanol extract.

| Comp # | µg/mL | % increase | µg/mL | % increase | Ratio | Comp Dose µg/mL | Additive (Calculated) | Observed |
|---|---|---|---|---|---|---|---|---|
| | P.G-1 | | T.C-3 | | | | | |
| C-44 | 0.67 | 0.90 | 0.33 | 2.33 | 2:1 | 1.0 | 3.23 | 31.57 |
| C-45 | 0.5 | 0.68 | 0.5 | 3.54 | 1:1 | 1.0 | 4.22 | 26.5 |
| | P.G-1 | | T.C-1 | | | | | |
| C-48 | 0.5 | 0.68 | 0.5 | 10.33 | 1:1 | 1.0 | 11.01 | 29.71 |
| | P.G-5 | | T.C-3 | | | | | |
| C-51 | 0.5 | 3.54 | 0.5 | 6.94 | 1:1 | 1.0 | 10.48 | 23.81 |
| C-52 | 0.33 | 2.33 | 0.67 | 9.29 | 1:2 | 1.0 | 11.62 | 26.35 |

TABLE 7-continued

Testosterone activity of the compositions containing *Punica granatum* peel ethanol or 50% aqueous ethanol or water extract and *Theobroma cacao* seed ethanol or water or 50% aqueous ethanol extract.

| Comp # | µg/mL | % increase | µg/mL | % increase | Ratio | Comp Dose µg/mL | Additive (Calculated) | Observed |
|---|---|---|---|---|---|---|---|---|
| | P.G-5 | | T.C-1 | | | | | |
| C-55 | 0.07 | 12.50 | 0.13 | 13.90 | 1:2 | 0.2 | 26.39 | 31.66 |
| | P.G-6 | | T.C-2 | | | | | |
| C-57 | 0.5 | 2.99 | 0.5 | 5.66 | 1:1 | 1.0 | 8.65 | 16.64 |

TABLE 8

Testosterone activity of the compositions containing *Punica granatum* peel methanol or 50% aqueous methanol or 50% aqueous acetone or ethyl acetate extract and *Theobroma cacao* seed 50% aqueous ethanol or water extract.

| Comp # | µg/mL | % increase | µg/mL | % increase | Ratio | Comp Dose µg/mL | Additive (Calculated) | Observed |
|---|---|---|---|---|---|---|---|---|
| | P.G-7 | | T.C-2 | | | | | |
| C-62 | 0.67 | 12.54 | 0.33 | 4.15 | 2:1 | 1.0 | 16.69 | 19.72 |
| C-63 | 2.5 | 14.47 | 2.5 | 0.99 | 1:1 | 5.0 | 15.46 | 23.95 |
| | P.G-8 | | T.C-1 | | | | | |
| C-67 | 1.67 | 6.44 | 3.33 | 6.24 | 1:2 | 5.0 | 12.68 | 28.55 |
| | P.G-10 | | T.C-1 | | | | | |
| C-71 | 0.13 | 12.95 | 0.07 | 8.04 | 2:1 | 0.2 | 20.99 | 33.59 |
| C-72 | 0.1 | 9.96 | 0.1 | 11.48 | 1:1 | 0.2 | 21.44 | 36.62 |
| C-73 | 0.07 | 6.97 | 0.13 | 14.92 | 1:2 | 0.2 | 21.89 | 33.69 |
| | P.G-11 | | T.C-1 | | | | | |
| C-74 | 3.33 | 31.06 | 1.67 | 3.13 | 2:1 | 5.0 | 34.19 | 38.59 |
| C-75 | 0.5 | 15.87 | 0.5 | 4.73 | 1:1 | 1.0 | 20.60 | 27.85 |

Example 21: General Procedure for Aromatase Inhibition Assay

Aromatase inhibition was determined using intact cells in culture as described by Samson et al., (Samson M. et al., *J. Steroid Biochem. Mol. Biol.* 2009, 116, 154-159) with modifications. Briefly, placental choriocarcinoma (JEG-3) cells (ATCC; Cat #HTB-36) were harvested from the culture flasks and 40000 cells/well were seeded in a 96-well plate in 200 µL of EMEM (Hi-Media; Cat #AL047S)+5% Charcoal-stripped FBS (Thermo Fisher; Cat #12676011) medium and incubated for 48 hours in a C02 incubator. After the incubation, older medium was replenished with 150 µL of fresh EMEM+5% Charcoal-stripped FBS medium. Cells were treated with different concentrations of test samples and incubated for 1 hour in a C02 incubator (pre-treatment). After the incubation, all the cells were treated with 50 nM 4-Androstene-3, 17-dione (Induction; Sigma Cat #46033-250 MG), a substrate for aromatase except for vehicle control (Cells+0.2% DMSO) and incubated for 48 hours in a C02 incubator. After 48 hours, the culture plate was centrifuged at 270×g for 10 minutes and the cell-free supernatants were collected and stored at −80° C. freezer until analysis. Enzyme immunoassay (EIA) was performed for Estrone using the EIA kit from Arbor assays (Cat #K031-H5) according to the manufacturer's protocol. Percent inhibition of aromatase was calculated by the following formula:

% Inhibition of Aromatase=[(Normalized Concn. of Estrone in Induction)−(Normalized Concn. of Estrone in Test samples)]/(Normalized Concn. of Estrone in Induction)×100. The results are presented in tables 9-13.

TABLE 9

Aromatase inhibitory activity of the compositions containing *Punica granatum* peel 70% ethanol extract and *Theobroma cacao* seed 50% aqueous ethanol extract.

| | P.G-4 | | T.C-2 | | | | % aromatase inhibition | |
|---|---|---|---|---|---|---|---|---|
| Comp # | µg/mL | % inhibition | µg/mL | % inhibition | Ratio | Comp Dose µg/mL | Additive (Calculated) | Observed |
| C-8 | 20.00 | 22.15 | 5.00 | 4.18 | 4:1 | 25.0 | 26.33 | 35.2 |
| C-9 | 3.75 | 14.41 | 1.25 | 5.39 | 3:1 | 5.0 | 19.8 | 26.46 |
| C-10 | 3.33 | 12.79 | 1.67 | 7.20 | 2:1 | 5.0 | 19.99 | 22.65 |
| C-11 | 0.5 | 0.33 | 0.5 | 7.08 | 1:1 | 1.0 | 7.41 | 21.56 |
| C-12 | 0.33 | 0.22 | 0.67 | 9.49 | 1:2 | 1.0 | 9.71 | 22.11 |
| C-13 | 0.25 | 0.17 | 0.75 | 10.63 | 1:3 | 1.0 | 10.8 | 26.95 |
| C-14 | 0.2 | 0.13 | 0.8 | 11.34 | 1:4 | 1.0 | 11.47 | 26.79 |

TABLE 10

Aromatase inhibitory activity of the compositions containing *Punica granatum* peel 70% ethanol extract and *Theobroma cacao* seed 90% aqueous ethanol or 70% aqueous ethanol extract.

| | | | | | | | % aromatase inhibition | |
|---|---|---|---|---|---|---|---|---|
| Comp # | µg/mL | % inhibition | µg/mL | % inhibition | Ratio | Comp Dose µg/mL | Additive (Calculated) | Observed |
| | P.G-4 | | T.C-4 | | | | | |
| C-15 | 0.8 | 12.88 | 0.2 | 3.64 | 4:1 | 1.0 | 16.52 | 20.6 |
| C-16 | 0.75 | 12.07 | 0.25 | 4.55 | 3:1 | 1.0 | 16.62 | 28.68 |
| C-18 | 0.5 | 8.05 | 0.5 | 9.1 | 1:1 | 1.0 | 17.15 | 26.8 |
| C-19 | 0.33 | 5.31 | 0.67 | 12.19 | 1:2 | 1.0 | 17.5 | 23.99 |
| C-20 | 0.25 | 4.02 | 0.75 | 13.65 | 1:3 | 1.0 | 17.67 | 37.52 |
| C-21 | 0.2 | 3.22 | 0.8 | 14.56 | 1:4 | 1.0 | 17.78 | 36.55 |
| | P.G-4 | | T.C-5 | | | | | |
| C-22 | 4.00 | 18.08 | 1.00 | 4.82 | 4:1 | 5.0 | 22.9 | 32.39 |
| C-23 | 3.75 | 16.95 | 1.25 | 6.02 | 3:1 | 5.0 | 22.97 | 31.07 |
| C-25 | 0.5 | 4.23 | 0.5 | 3.84 | 1:1 | 1.0 | 8.07 | 26.19 |
| C-26 | 0.33 | 2.79 | 0.67 | 5.14 | 1:2 | 1.0 | 7.93 | 25.94 |
| C-27 | 0.25 | 2.11 | 0.75 | 5.76 | 1:3 | 1.0 | 7.87 | 30.06 |
| C-28 | 0.2 | 1.69 | 0.8 | 6.14 | 1:4 | 1.0 | 7.83 | 30.17 |

TABLE 11

Aromatase inhibitory activity of the compositions containing *Punica granatum* peel 70% ethanol extract and *Theobroma cacao* seed aqueous methanol or 50% aqueous acetone or ethyl acetate extracts.

| | | | | | | | % Aromatase inhibition | |
|---|---|---|---|---|---|---|---|---|
| Comp # | µg/mL | % inhibition | µg/mL | % inhibition | Ratio | Comp Dose µg/mL | Additive (Calculated) | Observed |
| | P.G-4 | | T.C-6 | | | | | |
| C-29 | 3.33 | 1.59 | 1.67 | 5.27 | 2:1 | 5.0 | 6.86 | 24.8 |
| C-30 | 2.5 | 1.19 | 2.5 | 7.8 | 1:1 | 5.0 | 8.99 | 20.03 |
| C-31 | 1.67 | 0.80 | 3.33 | 10.39 | 1:2 | 5.0 | 11.19 | 18.89 |
| | P.G-4 | | T.C-7 | | | | | |
| C-34 | 8.33 | 9.26 | 16.67 | 6.48 | 1:2 | 25.0 | 15.74 | 23.59 |
| | P.G-4 | | T.C-8 | | | | | |
| C-35 | 3.33 | 1.59 | 1.67 | 2.78 | 2:1 | 5.0 | 4.37 | 27.22 |
| C-36 | 2.5 | 1.19 | 2.5 | 4.16 | 1:1 | 5.0 | 5.35 | 25.73 |
| C-37 | 1.67 | 0.80 | 3.33 | 5.55 | 1:2 | 5.0 | 6.35 | 20.88 |
| | P.G-4 | | T.C-9 | | | | | |
| C-39 | 0.5 | 3.58 | 0.5 | 6.78 | 1:1 | 1.0 | 10.36 | 29.88 |
| C-40 | 0.33 | 2.37 | 0.67 | 9.09 | 1:2 | 1.0 | 11.46 | 22.98 |
| | P.G-4 | | T.C-10 | | | | | |
| C-41 | 0.67 | 4.80 | 0.33 | 8.08 | 2:1 | 1.0 | 12.88 | 26.00 |
| C-42 | 0.5 | 3.58 | 0.5 | 12.24 | 1:1 | 1.0 | 15.82 | 31.88 |
| C-43 | 0.33 | 2.37 | 0.67 | 16.40 | 1:2 | 1.0 | 18.77 | 24.95 |

TABLE 12

Aromatase inhibitory activity of the compositions containing *Punica granatum* peel ethanol or 50% aqueous ethanol or water extract and *Theobroma cacao* seed ethanol or 50% aqueous ethanol extract.

| | | | | | | | % Aromatase inhibition | |
|---|---|---|---|---|---|---|---|---|
| Comp # | µg/mL | % inhibition | µg/mL | % inhibition | Ratio | Comp Dose µg/mL | Additive (Calculated) | Observed |
| | P.G-1 | | T.C-3 | | | | | |
| C-44 | 3.33 | 10.67 | 1.67 | 7.02 | 2:1 | 5.0 | 17.69 | 29.74 |
| C-45 | 2.5 | 8.01 | 2.5 | 10.50 | 1:1 | 5.0 | 18.51 | 30.75 |
| C-46 | 1.67 | 5.35 | 3.33 | 13.99 | 1:2 | 5.0 | 19.34 | 30.67 |
| | P.G-5 | | T.C-3 | | | | | |
| C-50 | 0.67 | 8.85 | 0.33 | 7.95 | 2:1 | 1.0 | 16.8 | 27.55 |
| C-51 | 0.5 | 6.60 | 0.5 | 12.05 | 1:1 | 1.0 | 18.65 | 27.19 |
| C-52 | 0.33 | 4.35 | 0.67 | 16.14 | 1:2 | 1.0 | 20.49 | 29.39 |
| | P.G-6 | | T.C-2 | | | | | |
| C-57 | 0.5 | 11.35 | 0.5 | 7.82 | 1:1 | 1.0 | 19.17 | 27.98 |
| C-58 | 8.33 | 9.00 | 16.67 | 15.35 | 1:2 | 25.0 | 24.35 | 29.16 |

TABLE 13

Aromatase inhibitory activity of the compositions containing Punica granatum peel methanol or 50% aqueous methanol or 50% aqueous acetone or ethyl acetate extract and Theobroma cacao seed 50% aqueous ethanol extract.

| Comp # | µg/mL | % inhibition | µg/mL | % inhibition | Ratio | Comp Dose µg/mL | % Aromatase inhibition Additive (Calculated) | Observed |
|---|---|---|---|---|---|---|---|---|
| | P.G-7 | | T.C-2 | | | | | |
| C-62 | 0.67 | 3.74 | 0.33 | 5.33 | 2:1 | 1.0 | 9.07 | 24.1 |
| C-63 | 0.5 | 2.79 | 0.5 | 8.07 | 1:1 | 1.0 | 10.86 | 21.34 |
| C-64 | 0.33 | 1.84 | 0.67 | 10.82 | 1:2 | 1.0 | 12.66 | 23.06 |
| | P.G-9 | | T.C-2 | | | | | |
| C-68 | 0.67 | 8.45 | 0.33 | 5.33 | 2:1 | 1.0 | 13.78 | 27.83 |
| C-69 | 0.5 | 6.30 | 0.5 | 8.07 | 1:1 | 1.0 | 14.37 | 25.93 |
| C-70 | 0.33 | 4.16 | 0.67 | 10.82 | 1:2 | 1.0 | 14.98 | 26.92 |

Example 22: Mitochondrial Biogenesis Assay

Mitochondrial biogenesis assay was performed by using an in-cell ELISA kit obtained from Abcam (Cambridge, UK; Cat #ab110217) following manufacturer's protocol. The levels of two mitochondrial proteins were measured simultaneously in each well. The two proteins are each subunits of a different oxidative phosphorylation enzyme complex, one protein being subunit I of Complex IV (COX-I), which is mitochondrial-DNA (mtDNA)-encoded, and the other being the 70 kDa subunit of Complex II (SDH-A), which is nuclear DNA (nDNA)-encoded. For the assay, rat skeletal (L6) cells (ATCC, Manassas, VA; Cat #CRL-1458) in DMEM medium (Sigma Cat #D7777) supplemented with 10% FBS were seeded (10000 cells/well) in a 96 well poly L-lysine coated plate and incubated overnight at 37° C. in a C02 incubator. Next day, the medium was removed and cells were treated with respective test samples at different concentrations. The treatment was repeated every day up to 3rd day. The culture wells receiving 0.2% DMSO were considered as vehicle control. After the treatment period, cells were fixed with 4% paraformaldehyde and probed with primary antibodies (COX-1 and SDH-A). Alkaline phosphatase (AP) and horse radish peroxidase (HRP)-labeled secondary antibodies were used for SDH-A and COX-1 respectively. Finally, AP/HRP development solution was added and measured the absorbance at 405 nm and 600 nm in a multi-mode spectrophotometer (Spectramax 2e). (COX-I) to (SDH-A) signal ratio was calculated for all the treatments for analysis of the effect of treatments. The percent increase of mitochondrial biogenesis over control was calculated using the following formula:

$$\frac{COX-1/SDH-A \text{ value of Treatment} - COX-1/SDH-A \text{ value of Treatment}}{COX-1/SDH-A \text{ value of Treatment}} \times 100$$

The results are presented in Table 14.

TABLE 14

Increase of mitochondrial biogenesis of the compositions containing Punica granatum peel 70% ethanol extract and Theobroma cacao seed water or 50% aqueous ethanol or 90% aqueous ethanol extract.

| Comp # | ng/mL | % increase | ng/mL | % increase | Ratio | Comp Dose ng/mL | % increase of mitochondrial biogenesis Additive (Calculated) | Observed |
|---|---|---|---|---|---|---|---|---|
| | P.G-4 | | T.C-1 | | | | | |
| C-1 | 8.0 | 1.87 | 2.0 | 1.21 | 4:1 | 10 | 3.08 | 8.52 |
| C-2 | 7.5 | 1.76 | 2.5 | 1.51 | 3:1 | 10 | 3.27 | 7.61 |
| C-3 | 6.67 | 1.56 | 3.33 | 2.01 | 2:1 | 10 | 3.57 | 5.07 |
| C-4 | 5.0 | 1.17 | 5.0 | 3.02 | 1:1 | 10 | 4.19 | 8.78 |
| C-5 | 3.33 | 0.78 | 6.67 | 4.03 | 1:2 | 10 | 4.81 | 8.11 |
| C-6 | 2.5 | 0.59 | 7.5 | 4.53 | 1:3 | 10 | 5.12 | 10.96 |
| C-7 | 2.0 | 0.47 | 8.0 | 4.83 | 1:4 | 10 | 5.30 | 9.76 |
| | P.G-4 | | T.C-2 | | | | | |
| C-8 | 8.0 | 4.14 | 2.0 | 1.91 | 4:1 | 10 | 6.05 | 7.63 |
| C-9 | 7.5 | 3.88 | 2.5 | 2.39 | 3:1 | 10 | 6.27 | 9.67 |
| C-11 | 50.0 | 2.61 | 50.0 | 0.98 | 1:1 | 100 | 3.59 | 7.67 |
| C-13 | 2.5 | 1.29 | 7.5 | 7.16 | 1:3 | 10 | 8.45 | 10.85 |
| | P.G-4 | | T.C-4 | | | | | |
| C-16 | 7.5 | 1.76 | 2.5 | 2.30 | 3:1 | 10 | 4.06 | 12.06 |
| C-17 | 6.67 | 1.56 | 3.33 | 3.06 | 2:1 | 10 | 4.62 | 14.91 |

Example 23: General Procedure for mTOR Phosphorylation Assay

Evaluation of mTOR phosphorylation in western blot assay: Rat L6 myoblasts ($6 \times 10^5$ cells/well in 2 mL) were seeded in 60 mm cell culture dishes and maintained in DMEM medium containing 10% FBS at 37° C. in a humidified atmosphere of 5% C02. Next day, cells were replaced with serum-free DMEM medium and maintained for another 18 hours. Cells were treated with different concentrations of test samples in serum-free DMEM medium (1 mL total volume) and incubated for 120 minutes at 37° C. in a C02 incubator. The 0.2% DMSO treated cells served as vehicle control.

Western blot: After the incubation, cell culture dishes were placed on ice tray and washed twice with 1×PBS. Seventy microliters of lysis buffer (10 mM Tris-HCl pH 7.4, 150 mM NaCl, 1 mM EDTA, 1 mM PMSF, 10 µg/mL Aprotinin, 10 µg/mL Leupeptin, 1% Triton X-100, 1 mM NaF, 1 mM $Na_3VO_4$, 0.5% Sodium deoxycholate, and 1 µM Pepstatin) was added to each culture dish and sonicated for 30 seconds. Following homogenization, samples were centrifuged at 16128×g for 10 minutes at 4° C. to sediment unbroken cells and nuclei. Supernatant was collected and protein was quantified using Pierce BCA protein assay kit (Thermo Scientific Cat #23225). SDS-PAGE was performed for the protein samples and resolved proteins were transferred onto nitrocellulose membrane using wet blotting method.

Briefly, 22 µg of protein was loaded onto acrylamide gel (7.5% resolving) and ran at 100V for approximately 1 hour 40 minutes. At the end of the run, proteins were transferred to the nitrocellulose membrane by placing transfer system at 4° C. chamber (100V for 2 hours). After the transfer, membrane was washed in 0.1M Tris-buffered saline containing 0.05% Tween20 (TBST) and blocked in Superblock blocking buffer (Thermo Scientific Cat #37535) with constant agitation for 30 minutes. The membrane was incubated with primary antibodies recognizing phospho-mTOR (Phosphorylation site: Ser2448; Cell Signaling Technology Cat #2971) and mTOR (Cell signaling Technology Cat #2983) proteins in TBST for 16 hours at 4° C. with agitation. Membrane was washed three times and incubated with peroxidase affinipure goat anti-rabbit secondary antibody (Jackson Immunoresearch Cat #111-035-045; 1:10000 dilution) for 1 hour at room temperature with agitation, followed by 3 times of washing in TBST for 5 minutes each. Immunoreactive bands were detected using a chemiluminiscent substrate (Thermo Scientific Cat #34080) and images were captured using Bio-Rad Molecular imager (Model: Chemi-DOC XRS+). Membrane was stripped of the phosphor-mTOR and mTOR antibodies and re-probed with anti-β-actin antibody (Sigma Cat #A4700-100 uL; 1:10000 dilution) by incubating at room temperature for 1 hour and images were captured. The intensities of phospho-mTOR and mTOR protein bands were calculated using Carestream MI software and normalized using β-Actin. mTOR activation was calculated by the ratio between phospho-mTOR (pmTOR) and mTOR band intensities. The relative mTOR activation by the individual ingredients or the compositions was calculated over the pmTOR/mTOR ratio obtained in the vehicle control. The increases of mTOR activation (pmTOR/mTOR) are presented in table 15.

TABLE 15

Increase of mTOR activation by the compositions containing *Punica granatum* peel 70% ethanol extract and *Theobroma cacao* seed 50% aqueous ethanol extract.

| | P.G-4 | | T.C-2 | | | | mTOR activation (% increase from control) | |
|---|---|---|---|---|---|---|---|---|
| Comp # | ng/mL | mTOR activation (% increase from control) | ng/mL | mTOR activation (% increase from control) | Ratio | Comp Dose ng/mL | Additive (Calculated) | Observed |
| C-8 | 80.0 | 1.80 | 20.0 | 0.79 | 4:1 | 100 | 2.59 | 16.09 |
| C-9 | 75.0 | 1.69 | 25.0 | 0.98 | 3:1 | 100 | 2.67 | 33.55 |
| C-10 | 66.7 | 1.50 | 33.3 | 1.31 | 2:1 | 100 | 2.81 | 25.26 |

Example-24: In Vivo Evaluation of Composition-77 (C-77) and Composition-78 (C-78) for Testosterone Boosting in Sprague Dawley Rats Methods: Male Sprague Dawley rats were acclimatized and 21 animals were randomized into three groups (G1 to G3). The treatment group animals were supplemented with C-77 (G2; 100 mg/kg) or C-78 (G3; 100 mg/kg; p.o.) once daily for 3 weeks all in 10 mL of vehicle (0.5% CMC sodium in water). The control group (G1) animals were supplemented with 10 mL of vehicle only. Blood samples were collected from all the animals; Serum separated and analyzed for testosterone levels by ELISA on day 22.

On the day of sacrifice, i.e., on day 22, animals were euthanized and caudal epididymides along with vas deferens (both side) were dissected out and semen squeezed out into Dulbecco's Phosphate Buffered Saline for semen analysis.

The results expressed as mean f S.E.M. Data were subjected to statistical analysis using one way ANOVA followed by Dunnett's post-hoc test to draw a comparison of all the groups with Normal control (G1) using GraphPad Prism v5.01 (GraphPad Software, Inc., CA, USA). P<0.05 was considered statistically significant. No abnormal clinical signs and weight difference were observed among all the groups throughout the treatment duration, indicating the safety of the test items, C-77 and C-78. The treatment groups displayed increased testosterone levels in serum samples of the day 22 over the control group. The testosterone levels exhibited by different treatment group are summarized in Table 16 and depicted in FIG. 1. Similarly, all the treatment groups showed improved semen parameters when compared to the control group as summarized in Table 17 and depicted in FIG. 2.

TABLE 16

Serum testosterone levels (ng/ml)

| Group | Dose (mg/kg, p.o.) | Testosterone (ng/mL) |
|---|---|---|
| G1-Normal Control | — | 0.45 ± 0.05 |
| G2 (C-77) | 100 | 0.71 ± 0.09* |
| G3 (C-78) | 100 | 1.15 ± 0.17* |

Data are expressed as mean ± S.E.M. n = 7;
*indicates significance (p < 0.05) vs. G1, One-way Anova followed by dunnett's post-hoc test Vs G1

TABLE 17

Semen parameters

| Group | Motility (%) | Count (millions/mL) | Live (%) | Normal morphology (%) |
|---|---|---|---|---|
| G1 (Vehicle Control) | 86 ± 2 | 29 ± 2 | 91 ± 1 | 92 ± 1 |
| G2 (C-77; 100 mg/kg) | 86 ± 3 | 30 ± 6 | 93 ± 1 | 93 ± 1 |
| G3 (C-78; 100 mg/kg) | 89 ± 4 | 35 ± 2 | 94 ± 1 | 95 ± 1 |

Data are expressed as mean ± S.E.M. n = 7

We claim:

1. A synergistic herbal composition comprising a combination of:
   a first ingredient comprising an ethanol or aqueous ethanol extract of a *Punica granatum* fruit rind; and
   a second ingredient comprising an ethanol or aqueous ethanol extract of a *Theobroma cacao* seed;
   wherein the synergistic herbal composition contains the combination in an amount effective for at least one of increasing testosterone levels, inhibiting aromatase activity, increasing mitochondrial biogenesis, and increasing mTOR activation in a patient in need thereof; and
   wherein the extract of the *Punica granatum* fruit rind and the extract of the *Theobroma cacao* seed are used in a ratio of 4:1 to 1:4 by weight.

2. The synergistic herbal composition as claimed in claim 1, wherein the first ingredient comprises an ethanol extract of the *Punica granatum* fruit rind.

3. The synergistic herbal composition as claimed in claim 1, wherein the first ingredient comprises an aqueous ethanol extract of the *Punica granatum* fruit rind.

4. The synergistic herbal composition as claimed in claim 1, wherein the second ingredient comprises an ethanol extract of the *Theobroma cacao* seed.

5. The synergistic herbal composition as claimed in claim 1, wherein the second ingredient comprises an aqueous ethanol extract of the *Theobroma cacao* seed.

6. The synergistic herbal composition as claimed in claim 1, wherein the herbal composition contains punicalagins in a concentration range of 0.1% to 20% by weight of the composition and theobromine in a concentration range of 0.1% to 10% by weight of the composition.

7. The synergistic herbal composition as claimed in claim 1, wherein the synergistic composition further comprises at least one additional component selected from the group consisting of a biological agent; a pharmaceutically acceptable active ingredient; a vitamin, a mineral; a pharmaceutically acceptable carrier; a nutraceutically acceptable carrier, a dietically acceptable excipient, and diluent.

8. The synergistic herbal composition as claimed in claim 7, wherein the pharmaceutically or nutraceutically or dietically acceptable excipient, carrier, or diluent is selected from the group consisting of monosaccharides, disaccharides, polysaccharides, dextrins, polyhydric alcohols, sugar alcohols, cellulose derivatives, silicates, metallic stearates, organic acids, fatty acid esters, polysorbate esters, natural gums, vitamins, amino acids, proteins, inorganic metal salts, natural pigments, flavors, preservatives, and mixtures thereof.

9. The synergistic herbal composition as claimed in claim 7, wherein the pharmaceutically or nutraceutically or dietically acceptable excipient, carrier, or diluent is selected from the group consisting of glucose, dextrose, fructose, galactose, sucrose, maltose, lactose, lactulose, trehalose, cellobiose, chitobiose, starch, modified starch, sodium starch glycolate, pregelatinized starch, soluble starch, yellow dextrin, white dextrin, maltodextrin, sorbitol, mannitol, inositol, xylitol, isomalt, microcrystalline cellulose, hydroxypropyl methyl cellulose, hydroxy ethyl cellulose, magnesium aluminum metasilicate, magnesium aluminum silicate, talc, colloidal silicon dioxide, calcium stearate, magnesium stearate, zinc Stearate, citric acid, tartaric acid, malic acid, succinic acid, lactic acid, L-ascorbic acid, fatty acid esters, polysorbate esters, acacia gum, carrageenan gum, guar gum, xanthan gum, B group vitamins, amino acids, casein, gelatin, pectin, agar, sodium chloride, calcium chloride, dicalcium phosphate, zinc sulphate, and zinc chloride.

10. The synergistic herbal composition as claimed in claim 7, wherein the herbal composition is formulated into a dosage form selected from the group consisting of a dry powder, a liquid, a beverage, a food product, a dietary supplement, a tablet, a capsule, a chewable tablet, and a candy.

11. The synergistic herbal composition as claimed in claim 7, wherein the composition is formulated into a nutritional or dietary supplement selected from the group consisting of a food, a solid chocolate bar, a solid nutritional bar, a solid snack bar, a semisolid food, a cream, a jam, a gel, a beverage, a beverage containing lactic acid bacteria, a drop, a candy, a chewing gum, gummy candy, a yoghurt, an ice cream, a pudding, a soft adzuki bean jelly, a jelly, a cookie, a tea, a soft drink, a juice, milk, coffee, a cereal, and combinations thereof.

12. A dosage form comprising the synergistic herbal composition according to claim 1.

13. A method of increasing testosterone levels, inhibiting aromatase activity, increasing mitochondrial biogenesis, and/or increasing mTOR activation in a patient in need thereof, wherein the method comprises administering the synergistic herbal composition according to claim 1 to the patient.

* * * * *